(12) United States Patent
Van Den Aardweg

(10) Patent No.: US 9,649,050 B2
(45) Date of Patent: May 16, 2017

(54) METHOD AND APPARATUS FOR ESTIMATING RESPIRATORY IMPEDANCE

(75) Inventor: Joost Gerard Van Den Aardweg, Heemstede (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 925 days.

(21) Appl. No.: 13/511,207

(22) PCT Filed: Nov. 24, 2010

(86) PCT No.: PCT/IB2010/055392
§ 371 (c)(1),
(2), (4) Date: May 22, 2012

(87) PCT Pub. No.: WO2011/067698
PCT Pub. Date: Jun. 9, 2011

(65) Prior Publication Data
US 2012/0289852 A1  Nov. 15, 2012

(30) Foreign Application Priority Data

Dec. 3, 2009 (EP) .................................... 09177892

(51) Int. Cl.
*A61B 5/085* (2006.01)
*A61B 5/00* (2006.01)

(52) U.S. Cl.
CPC ............ *A61B 5/085* (2013.01); *A61B 5/7257* (2013.01)

(58) Field of Classification Search
CPC ...... A61B 5/085; A61B 5/7257; A61B 5/7253
(Continued)

(56) References Cited

U.S. PATENT DOCUMENTS 5,318,038 A  *  6/1994 Jackson et al. ................ 600/533
5,555,880 A  *  9/1996 Winter et al. ............ 128/204.21
(Continued)

FOREIGN PATENT DOCUMENTS

CN    1767785 A    5/2006
JP    1972631 A    5/2007
(Continued)

OTHER PUBLICATIONS

Pedro Lopes De Melo, "New Impedance Spectrometer for Scientific and Clinical Studies of the Respiratory System", Review of Scientific Instruments, vol. 71, No. 7, Jul. 2000, pp. 2867-2872.
(Continued)

*Primary Examiner* — Patricia Mallari
*Assistant Examiner* — Michael Catina
(74) *Attorney, Agent, or Firm* — Michael W. Haas

(57) ABSTRACT

The acoustic impedance of the respiratory system can be inferred from oscillations that are generated in an airway of a subject. The impedance describes the frequency-dependent relation between the resulting oscillations in flow and pressure. When the impedance varies from inspiration to expiration, it has to be estimated with a high time resolution. A method is provided that reliably estimates the impedance in time intervals that are short enough for physiological purposes. A simple version of the uncertainty principle has been derived for discrete time and frequency. A discrete time-frequency transform has been developed that gives an optimal time-frequency resolution according to this principle. The transform is orthonormal, which permits an analysis of variance in the discrete time-frequency domain. The impedance follows from bivariate least-squares analysis in the time-frequency domain, under the assumption that noise is present in both flow and pressure.

19 Claims, 12 Drawing Sheets

(58) Field of Classification Search
USPC .................................................. 600/529, 533
See application file for complete search history.

(56) References Cited

U.S. PATENT DOCUMENTS

| | | | |
|---|---|---|---|
| 5,795,304 A * | 8/1998 | Sun .................... | A61B 5/04884 600/546 |
| 5,885,225 A | 3/1999 | Keefe et al. | |
| 6,066,101 A | 5/2000 | Johnson | |
| 6,142,952 A * | 11/2000 | Behbehani et al. .......... | 600/533 |
| 6,699,204 B1 * | 3/2004 | Kehyayan .............. | A61B 7/003 600/529 |
| 2008/0114261 A1 * | 5/2008 | Dellaca et al. ............... | 600/529 |

FOREIGN PATENT DOCUMENTS

| | | |
|---|---|---|
| JP | 2009240752 A | 10/2009 |
| WO | WO2004066804 A2 | 8/2004 |
| WO | WO2005104944 A1 | 11/2005 |

OTHER PUBLICATIONS

K.A. Davis et al, "Time Series Versus Fourier Transform Methods for Estimation of Respiratory Impedance Spectra", Int. J. Biomed Comput. 27 (1991), pp. 261-276.

J.G. Van Den Aardweg et al, "Blood Pressure and Heart Rate Variability Explained by Chemoreceptor Reflexes in the Obstructive Sleep Apnea Syndrome", Annual International Conference of the IEEE Engineering in Medicine and Biology Society, vol. 12, No. 5, 1990, pp. 2049-2050.

R.L. Dellaca et al, "Expiratory Flow Limitation Detected by Forced Oscillation and Negative Expiratory Pressure", European Respiratory Journal, vol. 29, No. 2, pp. 263-274.

Forbes et al, "Consistent Analogs of the Fourier Uncertainty Relation", Am J. Phys., vol. 69, No. 10, 2001, pp. 1091-1095.

Fan-Liang, "Development of Non-Invasive Instrument for Measuring Respiratory Acoustical Impedance by Spectral Analysis", Chinese Journal of Biomedical Engineering, vol. 11, No. 4, Dec. 1992, pp. 238-251.

Daroczy et al, "An Improved Forced Oscillatory Estimation of Respiratory Impedance", Int J Biomed Comput, vol. 13, 1982, pp. 221-235.

Gabor, "Theory of Communication", J Inst Electr Eng, vol. 93, 1946, pp. 429-457.

Forbes et al, "Uncertainty Relations and Minimal Uncertainty States for the Discrete Fourier Transform and the Fourier Series", Journal of Physics A: Mathematical and General, vol. 36, 2003, pp. 7027-7047.

Anderson, "Distribution of the Serial Correlation Coefficient", Annals of Mathematical Statistics, vol. 13, 1942, pp. 1-13.

Bijaoui et al, "Mechanical Output Impedance of the Lung Determined From Cardiogenic Oscillations", J Appl Physiol, vol. 91, 2001, pp. 859-865.

Farre et al, "Estimation of Random Errors in Respiratory Resistance and Reactance Measured by the Forced Oscillation Technique", European Respiratory Journal, vol. 10, 1996, pp. 685-689.

Kaczka et al, "Technique to Determine Inspiratory Impedance During Mechanical Ventilation: Implications for Flow Limited Patients", Annals of Biomedical Engineering, vol. 27, 1999, pp. 340-355.

Michaelson et al, "Pulmonary Mechanics by Spectral Analysis of Forced Random Noise", Journal of Clinical Investigation, vol. 56, 1975, pp. 1210-1230.

Oostveen et al, "The Forced Oscillation Technique in Clinical Practice: Methodology, Recommendations and Future Developments", Eur. Respir. J, 2003, pp. 1026-1041.

Dickinson, Eigenvectors and Functions of the Discrete Fourier Transform, IEEE Transactions on Acoustics, Speech and Signal Processing, vol. ASSP-30, No. 1, 1982, pp. 25-31.

Dellaca et al, "Detection of Expiratory Flow Limitation in COPD Using the Forced Oscillation Technique", European Respiratory Jjournal, vol. 23, 2004, pp. 232-240.

Delavault et al, "Characterization and Validation of Forced Input Method for Respiratory Impedance Measurement", Respiration Physiology, vol. 40, 1980, pp. 119-136.

Franken et al, "Systematic and Random Errors in the Determination of Respiratory Impedance by Means of the Forced Oscillation Technique: A Theoretical Study", IEEE Transactions on Biomedical Engineering, vol. BME-30, No. 10, Oct. 1983, pp. 642-651.

Horowitz et al, "Computation of Respiratory Impedance From Forced Sinusoidal Oscillations During Breathing", Computers and Biomedical Research, vol. 16, 1983, 499-521.

Landser et al, "Errors in the Measurement of Total Respiratory Resistance and Reactance by Forced Oscillations", Respiration Physiology, vol. 28, 1976, pp. 289-301.

Macleod et al, "Respiratory Input Impedance Measurement: Forced Oscillation Methods", Medical & Biological Engineering & Computing, vol. 39, 2001, pp. 505-516.

Olkkonen, "Running Discrete Fourier Transform for Time-Frequency Analysis of Biomedical Signals", Med. Eng. Phys. vol. 17, No. 6, 1995, pp. 455-458.

Opatrny, "Number-Phase Uncertainty Relations", J. Phys. A: Math. Gen, vol. 28, 1995, pp. 6961-6975.

Venkatesh et al, "On the Uncertainty Inequality as Appiled to Discrete Signals", International Journal of Mathematics and Matematical Sciences, Article ID 48185, 2006, pp. 1-22.

Welch, "The Use of Fast Fourier Transform for the Estimation of Power Spectra: A Method Based on Time Averaging Over Short, Modified Periodotrams", IEEE Transactions on Audio and Electroacoustics, vol. AU-15, No. 2, 1967, pp. 70-76.

Mc Call et al, "Harmonic Content of Certain Respiratory Flow Phenomena of Normal Individuals", J. Appl. Physiol. vol. 10, 1957, pp. 215-218.

Dubois, "Oscillation Mechanics of Lungs and Chest in Man", J. Appl. Physiol., vol. 8, 1967, pp. 587-594.

Blackstock, "Fundamentals of Physical Acoustics", University of Texas, A Wiley-Intersscience Publication, New York, 2000, pp. 36-144.

Shizhong, J. et al., "Identification of Respiratory Mechanics Parameters by Applying Forced Oscillation Methods", Journal of the Fourth Military Medical University, vol. 6, No. 1, Dec. 31, 1985, pp. 67-76.

Hua, Wang et al., "Estimation of the Degree of Airflow Obstruction for Severe COPD Patient and Affects of Non-Invasive Positive Pressure Ventilation", Chinese Journal of Respiratory and Critical Care Medicine, vol. 8, No. 2, Mar. 31, 2009, pp. 156-162.

Min, Huang et al., "Measuring Respiratory Ventilation Function with Forced Oscillation Methods", Chinese Journal of Medicine Instrumentation, vol. 14, No. 6, Dec. 31, 1990, pp. 345-360.

\* cited by examiner

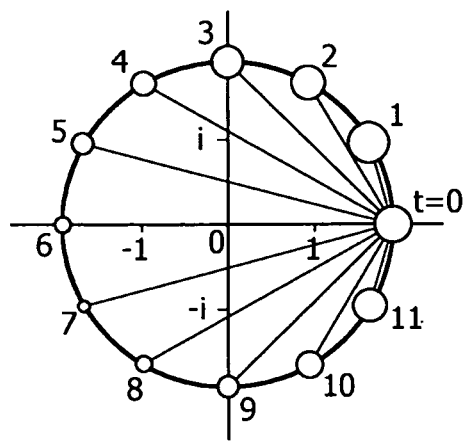
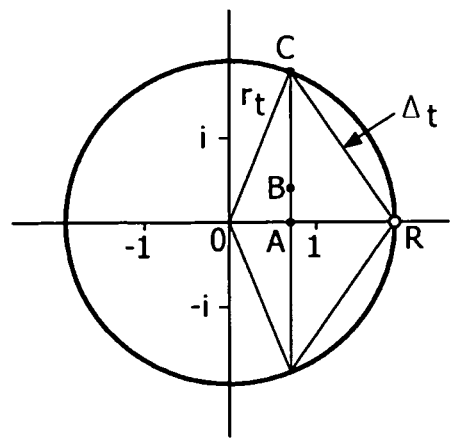
FIG. 3A  FIG. 3B
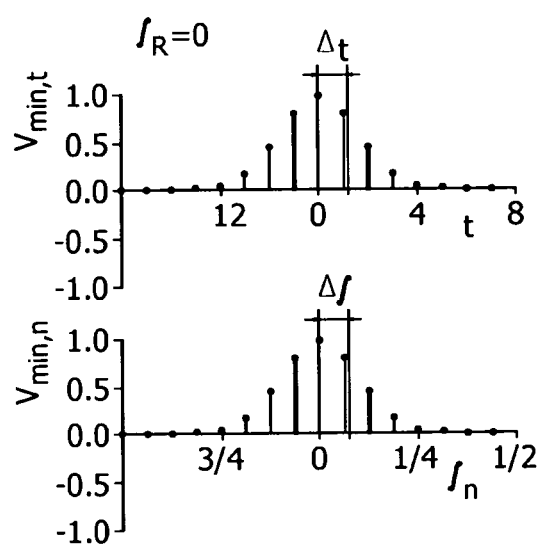
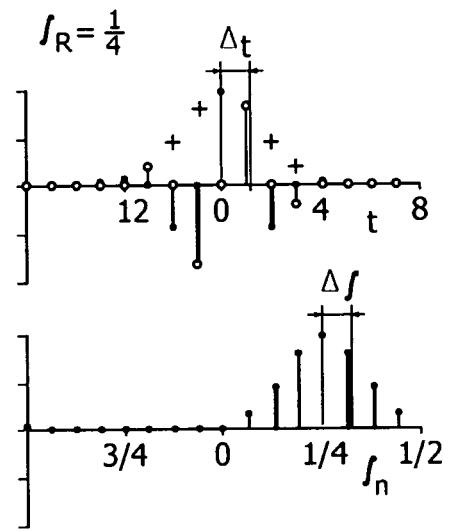
FIG. 4A  FIG. 4B

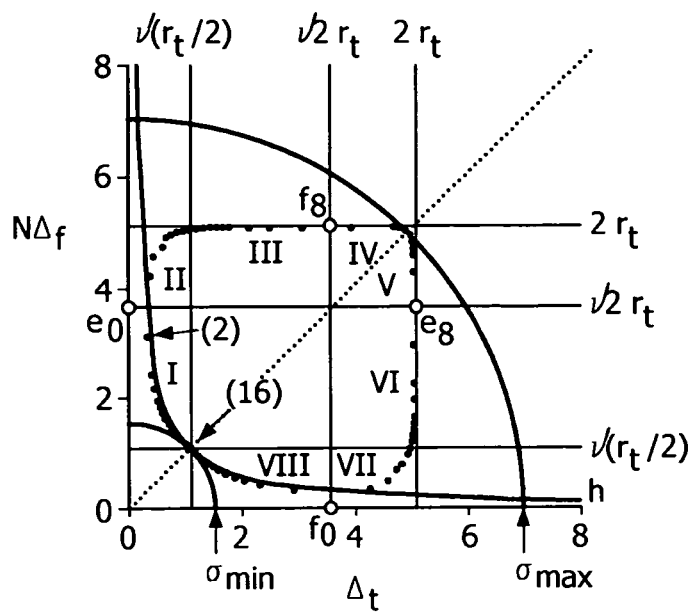
FIG. 15
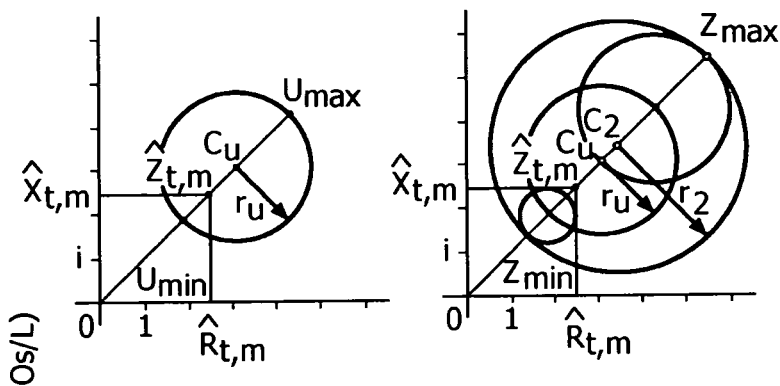
FIG. 16A    FIG. 16B
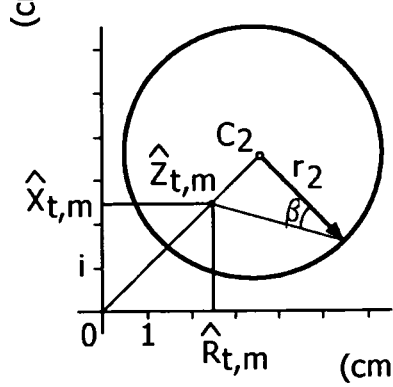 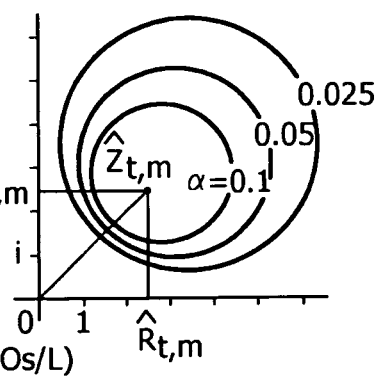
FIG. 16C    FIG. 16D

METHOD AND APPARATUS FOR ESTIMATING RESPIRATORY IMPEDANCE

TECHNICAL FIELD OF THE INVENTION

The invention relates to a method and apparatus for estimating respiratory impedance from forced pressure oscillations.

BACKGROUND TO THE INVENTION

The respiratory or acoustic impedance of a human respiratory system can be measured to obtain information concerning the resistance, compliance and inertia of the airways, lungs and chest wall. This information is useful in diagnosing the nature and severity of a variety of respiratory diseases such as chronic obstructive pulmonary disease (COPD), asthma and bronchitis.

In a forced oscillation technique (FOT), such as that described in "Expiratory Flow Limitation Detected by Forced Oscillation and Negative Expiratory Pressure" by Dellacà et al., pages 363-374 European Respiratory Journal Vol. 29 No. 2 (reference 1), acoustic waves are directed into the respiratory system while the person breathes normally, and the response is measured to determine the respiratory impedance.

The respiratory impedance describes the frequency-dependent relation in the oscillations resulting from the acoustic waves in terms of flow and pressure. Where the respiratory impedance varies from inspiration to expiration (as in some diseases and other medical conditions), the respiratory impedance must be estimated with a fine time resolution. However, in the prior art, little consideration has been given to the reliability of techniques for estimating the respiratory impedance in time intervals that are short enough for physiological purposes (i.e. shorter than the duration of an inhalation or exhalation).

Therefore, there is a need for a method and apparatus for reliably estimating the respiratory impedance in short time intervals.

SUMMARY OF THE INVENTION

According to a first aspect of the invention, there is provided a method of estimating respiratory impedance, the method comprising generating pressure waves in a patient interface device in communication with an airway of a subject; determining the flow and pressure of the gas in a pneumatic system that includes the patient interface device and an airway of such a subject to produce respective time series representing the flow and pressure; transforming the respective time series to the time-frequency domain to create a transformed time series; estimating the power of the flow and pressure from the respective transformed time series; estimating respective cross spectra of the flow and pressure based on the transformed time series; and estimating the respiratory impedance of the subject from the estimated power and cross spectra.

According to a second aspect of the invention, there is provided an apparatus for estimating respiratory impedance, the apparatus comprising a patient interface device; an exitation source for generating oscillating pressure, flow, or volume of gas in such an airway of such a subject; means for determining the flow and pressure of gas in a pneumatic circuit defined by the patient interface device and an airway of such a subject and for outputting respective time series of values representing the flow and pressure; a processor configured to transform the respective time series to the time-frequency domain; estimate a power of the flow and the pressure from the respective transformed time series; estimate respective cross spectra of the flow and pressure based on the respective transformed time series; and estimate the respiratory impedance of the subject from the estimated power and cross spectra.

According to a third aspect of the invention, there is provided a computer program product comprising a computer readable medium with computer readable code embodied therein, the computer readable code being configured such that, on execution by a suitable processor or computer, the processor or computer performs the method described above.

The estimate of respiratory impedance may be made by a diagnostic tool that uses the estimate to assess obstruction of the airways or to estimate the severity of disease. The diagnostic tool may therefore also be used to assess the effectiveness of treatments (whether pharmacological or otherwise) that should affect the respiratory impedance.

Thus, according to a fourth aspect of the invention, there is provided a method of diagnosing a physiological condition, the method comprising measuring respiratory impedance as described above, and diagnosing a physiological condition on the basis of the measured respiratory impedance.

The estimates of respiratory impedance may also or alternatively be used to adapt the settings of machine used in the treatment of a medical condition, for example a non-invasive ventilator that is used for counteracting airway obstruction, or in determining a treatment regimen (for example which particular medication or device to use, the medication dosage, etc.) for the physiological condition.

Thus, according to a fifth aspect of the invention, there is provided a method of treatment of a physiological condition, the method comprising measuring respiratory impedance as described above, and determining and/or administering a treatment for the physiological condition on the basis of the measured respiratory impedance.

BRIEF DESCRIPTION OF THE DRAWINGS

Preferred embodiments of the invention will now be described in detail, by way of example only, with reference to the following drawings, in which:

FIGS. 3A and 3B illustrate the circularity assumption and the uncertainty in the discrete time domain respectively;

FIGS. 4A and 4B illustrate time series for which $\Delta_t^2 + N^2 \Delta_f^2$ is minimal;

FIG. 15 illustrates the uncertainty in the plot of $N\Delta_f$ vs. $\Delta_t$ for N=16;

FIG. 16 illustrates the estimation of 100(1−α) % confidence limits for $\hat{Z}_{t,m}$ in the complex plane;

DETAILED DESCRIPTION OF THE PREFERRED EMBODIMENTS

As described above, the acoustic impedance of the respiratory system can be inferred from forced pressure oscillations in a mouthpiece or facemask (forced oscillation technique, FOT). Since this 'respiratory impedance' depends on resistance, compliance and inertia of the airways, lungs and chest wall, it provides insight into the nature and severity of a variety of respiratory diseases. The frequency-dependent impedance is often variable in time. In chronic obstructive pulmonary disease, airway resistance usually increases during expiration. In sleep apnea or snoring, resistance may increase during inspiration. This asks for a reliable estimation of impedance in short time intervals, shorter than the duration of a breath.

Respiratory impedance is defined as the complex-valued transfer function that describes a linear relation between flow q and pressure p as a function of frequency f, $$p(f)=q(f)z(f), \quad (1)$$

where the impedance is denoted by z(f). This equation only holds if z(f) is constant and time is infinite. If the system is temporarily stable, z(f) may still be estimated in a short time interval. This is limited, however, by the uncertainty principle, which says that a signal cannot be sharply localized in both the time and frequency domains. In addition, the use of short time intervals makes the estimation increasingly dependent on chance events. The question is how this would affect the estimation of a transfer function like z(f), which may only be stable in a part of the respiratory cycle.

In the following, the transfer function of a temporarily stationary process is estimated by linear regression in the discrete time-frequency domain. An uncertainty relation is derived for discrete time and frequency, which is used to obtain an optimal time-frequency resolution. Analysis of the statistical properties of the used impedance estimator yields a frequency-dependent parameter of respiratory mechanics, of which both the estimated values and the confidence limits can be followed in time.

A table (Table 1) is included at the end of the Detailed Description which provides a glossary of symbols and abbreviations used in the following explanation of the invention.

Methods

This section of the Detailed Description sets out the mathematical basis for the method and apparatus according to the invention. A less mathematical explanation of the invention is provided in the "Discussion" section below.

Figure 1:
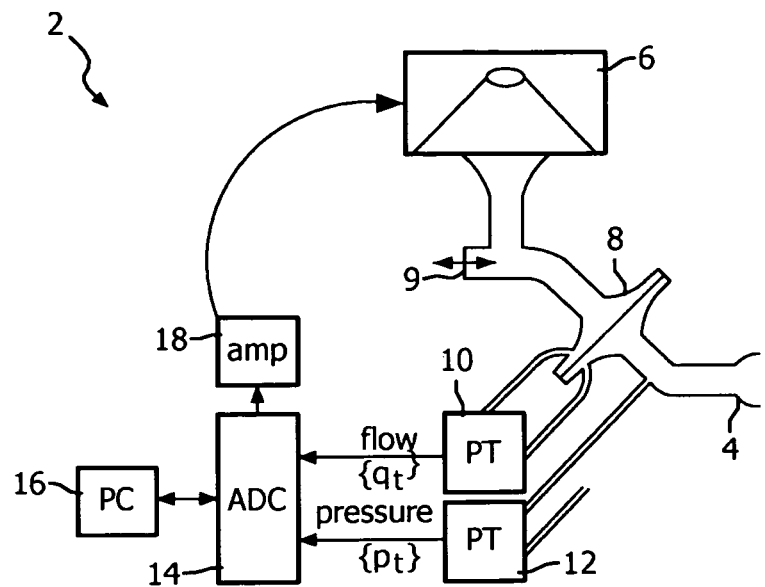
FIG. 1 is a block diagram of an apparatus for estimating the respiratory impedance from forced pressure oscillations in accordance with the invention.

A schematic diagram of an apparatus 2 according to the invention is shown in FIG. 1. Briefly, the used FOT device 2 consists of a patient interface device 4 connected to an airway of a subject to create a pneumatic system that includes an airway of such a subject. Patient interface device 4 is any device suitable to provide a pneumatic connection with the airway of a subject, such a mask or mouthpiece. Patient interface device 4 is operatively coupled to an excitation source 6 that generates pressure waves, flow changes, or volume changes with relatively low frequencies, for example frequencies from 8 to 24 Hz. In an exemplary embodiment of the present invention, patient interface device 4 is a loudspeaker.

In the illustrated embodiment, a patient breathes air through a mesh-wired resistance 9 that is near to pneumotach head 8, which is located between the patient interface device 4 and exitation source 6. The forced waves are partly reflected in the airways and lungs of the patient and lead to oscillations in airflow and pressure which are measured in the FOT device 2. The airflow through the pneumotach head 8 is measured using a differential pressure transducer 10 and the pressure is measured using a second pressure transducer 12 near to the mouthpiece 4. An analog-to-digital convertor 12 yields respective time series of flow and pressure, $\{q_t\}$ and $\{p_t\}$, where the integer t is the discrete time index, which are provided to a processor or computer 16 for analysis. The computer or processor 16 can also provide the signals for controlling the frequency of the acoustic waves generated by the loudspeaker 6 via the analog-to-digital convertor 14 and an amplifier 18. Further details of a specific embodiment of the apparatus 2 are provided in the section below entitled "The measurement apparatus".

The present invention also contemplates that other gas flow delivery devices can be coupled to the airway of the subject in addition to excitation source 6. For example, a pressure support system or ventilator can be coupled to patient interface device 4 to provide a flow of gas, for example, while excitation source 6 oscillates the airway of the subject. It should also be noted that the flow and pressure measurements can be made at any location along the pneumatic system, including measuring the pressure and flow within the pressure support system or ventilator. The measured pressure and flow can then be used to determine the flow and pressure of the gas in the pneumatic system, such as at the airway of the patient, using any conventional technique.

The present invention also contemplates that excitation source 6 can be a components of the pressure support system or the ventilator rather than a stand-alone apparatus. For example, a pressure support system or ventilator may include a valve to control the flow/pressure of gas delivered to the patient. The present invention contemplates oscillating such a valve to produce the low frequency pressure waves, flow changes, or volume changes. Of course, any other device or system that is capable of generating the low frequency pressure waves, flow changes, or volume changes, such as a piston, can be used as excitation source 6.

Rather than measuring pressure and/or flow using a pressure and/or flow sensors, the present invention also contemplates that the flow or the pressure can be set or controlled, such as by the pressure support system or ventilator. In which case, the set pressure or the set flow is used as the flow of pressure for present purposes rather than the output of differential pressure transducer 10 or second pressure transducer 12.

The interval between two samples (in seconds) is the reciprocal of the sample rate (in Hz). In this section, the time- and frequency-dependent impedance is derived from these time series, using relatively simple linear algebra. The reader who is not familiar with linear algebra is referred to the Discussion section below, where the main results are summarized in words.

A Simple Linear Model.

Figure 2:
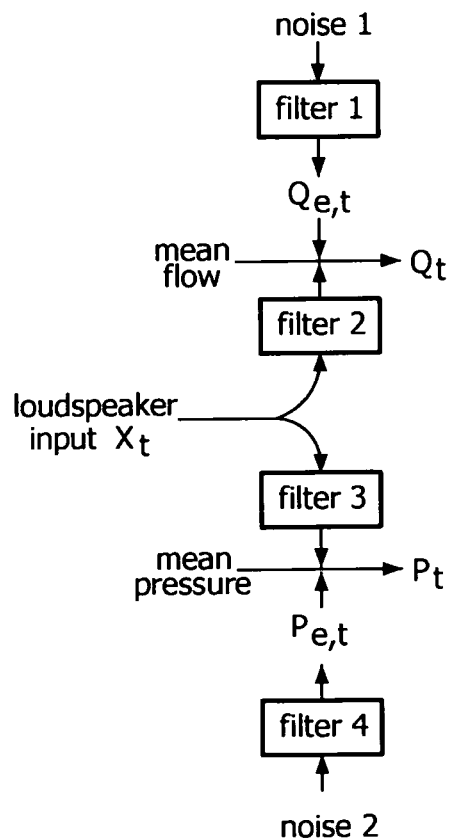
FIG. 2 is a schematic diagram of the linear model used to estimate the respiratory impedance in accordance with the invention.

To account for chance events, assume that the bivariate time series $\{q_t, p_t\}$ is a realization of the bivariate stochastic process $\{Q_t, P_t\}$. Deterministic variables are written in lowercase and random variables (RVs) in uppercase. Further assume that time is infinitely long (t= ..., −1, 0, 1, ...). Referring now to FIG. 2, the excitation source input $x_t$ is filtered through linear time-invariant filters (2 and 3) with impulse response sequences $\{h_{qx,l}\}$ and $\{h_{px,l}\}$. This gives flow and pressure as predicted by the linear model, $$q_{p,t} \equiv \sum_{l=0}^{\infty} h_{qx,l} x_{t-l} \text{ and } p_{p,t} \equiv \sum_{l=0}^{\infty} h_{px,l} x_{t-l}. \qquad (2)$$

Suppose that these 'true' values are disturbed by two independent sources of zero mean white noise with respective variances $\sigma_Q^2$ and $\sigma_P^2$. These sources of noise are also passed through linear time-invariant filters (1 and 4) to give the 'error' terms $Q_{e,t}$ and $P_{e,t}$. The complete model is then written as $$\begin{cases} Q_t = \mu_Q + q_{p,t} + Q_{e,t} \\ P_t = \mu_P + p_{p,t} + P_{e,t} \end{cases} \qquad (3)$$

where the mean values $\mu_Q$ and $\mu_P$ are constants. Since the resulting $Q_t$ and $P_t$ are normally distributed, the supposed bivariate process $\{Q_t, P_t\}$ is completely stationary.

The Circularity Assumption.

While the described stationary process is infinitely long, it is an aim of the invention to describe transient phenomena, where stationary can only be assumed for a finite sequence of N events. This can be solved by assuming that time is circular, in the sense that the last event precedes the first. The resulting time series may then be represented by placing the N events at regular intervals along a circle, like a clock. One can endlessly pursue the circle in the same direction without leaving it. The resulting infinite time series is periodic in N. That is, for any integer j, $$x_t = x_{t+jN}. \qquad (4)$$

Substituting u=t−l+j N, the first convolution in Eq. 2 can be rewritten as $$q_{p,t} = \sum_{u=0}^{N-1} \sum_{j=-\infty}^{\infty} h_{qx,t-u+jN} x_{u-jN}.$$

Due to the supposed periodic character of $x_t$ (Eq. 4), $x_{u-jN} = x_u$. The infinite sum in the above equation can be defined as $h_{qx,t-u}$ 'periodized to length N', denoted by $$h^o_{qx,t-u} \equiv \sum_{j=-\infty}^{\infty} h_{qx,t-u+jN}. \qquad (5)$$

As a result, $$q_{p,t} = \sum_{u=0}^{N-1} h^o_{qx,t-u} x_u. \qquad (6)$$

Since $h^o_{qx,t-u}$ is also periodic in N, the index t−u can be augmented with N if t−u is negative (so that the index always falls in the range from zero to N−1, which is convenient). When the sequences are represented by column vectors, Eq. 6 can also be written as (if N=4)

$$\begin{bmatrix} q_{p,0} \\ q_{p,1} \\ q_{p,2} \\ q_{p,3} \end{bmatrix} = \begin{bmatrix} h^o_{qx,0} & h^o_{qx,3} & h^o_{qx,2} & h^o_{qx,1} \\ h^o_{qx,1} & h^o_{qx,0} & h^o_{qx,3} & h^o_{qx,2} \\ h^o_{qx,2} & h^o_{qx,1} & h^o_{qx,0} & h^o_{qx,3} \\ h^o_{qx,3} & h^o_{qx,2} & h^o_{qx,1} & h^o_{qx,0} \end{bmatrix} \begin{bmatrix} x_0 \\ x_1 \\ x_2 \\ x_3 \end{bmatrix}. \qquad (7)$$

The N×N matrix in this equation is a circulant (a square matrix whose rows are right-shifted versions of the previous row, with wraparound at the edges). When the first row is denoted by $h_{qx}^H$, where the superscript H stands for the Hermitian transpose, the circulant may also be written as $\text{circ}\{h_{qx}^H\}$. Let $x \equiv \{x_0, \ldots, x_{N-1}\}$, $C_{qx} \equiv \text{circ}\{h_{qx}^H\}$ and $q_p \equiv \{q_{p,0}, \ldots, q_{p,N-1}\}$. Then $q_p = C_{qx} x$. Similarly, $p_p = C_{px} x$, so that Eq. 3 becomes $$\begin{cases} Q = \mu_Q + q_p + Q_e \\ P = \mu_P + p_p + P_e \end{cases}, \text{ or} \qquad (8)$$

$$\begin{cases} Q = \mu_Q + C_{qx} x + Q_e \\ P = \mu_P + C_{px} x + P_e. \end{cases}$$

The Discrete Frequency Domain.

To derive the frequency-dependent impedance, the model of Eq. 8 has to be transformed to the discrete frequency domain. As a step-up to time-frequency analysis, this is briefly summarized here. Transformation of a given time series $x \equiv \{x_0, \ldots, x_{N-1}\}$ to the discrete frequency domain partitions the series into a set of harmonic oscillations with discrete frequencies $f_n \equiv n/N$, for n=0, ..., N−1. Such an oscillation is described by the N-vector $$f_n = \{1, \omega^n, \omega^{n \cdot 2}, \ldots, \omega^{nt}, \ldots, \omega^{n(N-1)}\}, \qquad (9)$$

where $\omega \equiv \exp(2\pi i/N)$ and $i^2 = -1$. Due to Euler's theorem, $$\exp(2\pi i nt/N) = \cos(2\pi nt/N) + i \sin(2\pi nt/N), \qquad (10)$$

so that the vector $f_n$ actually describes a combined oscillation along the real and imaginary axis with frequency $f_n$. It is readily shown that $$f_n^H f_{n'} = \begin{cases} N, & n = n'; \\ 0, & n \neq n'. \end{cases} \qquad (11)$$

As a result, the squared norm $\|f_n\|^2 = f_n^H f_n$ equals N, while two oscillations at different harmonic frequencies are orthogonal.

Transformation of x to the discrete frequency domain is performed by the 'orthonormal discrete Fourier transform' (ODFT) matrix F, defined as $$F \equiv \frac{1}{\sqrt{N}}\{\omega^{-nt}\} = \frac{1}{\sqrt{N}}\begin{bmatrix} f_0^H \\ \vdots \\ f_{N-1}^H \end{bmatrix}, \quad (12)$$

where n,t=0, ..., N−1. This transform yields the N-vector F x, whose components are the inner products $f_n^H x/\sqrt{N}$. From Eq. 11, it follows that the rows (and columns) of F are orthonormal so that the matrix is unitary, $$FF^H = F^H F = I, \quad (13)$$

where I is the N×N identity matrix. This permits a synthesis of x from the N oscillations, $$x = Ix = F^H F x = \frac{1}{N}[f_0 \cdots f_{N-1}]\begin{bmatrix} f_0^H \\ \vdots \\ f_{N-1}^H \end{bmatrix} x = \frac{1}{N}\sum_{n=0}^{N-1} f_n(f_n^H x). \quad (14)$$

Accordingly, x is written as the weighted sum of N harmonic oscillations with frequencies $f_n$.

The vectors $f_n$ are eigenvectors of circulant matrices, so that we can write $$C_q f_n = f_n H_{qx,n}. \quad (15)$$

The complex number $H_{qx,n}$ is the transfer function from x to q for frequency $f_n$, defined as $$H_{qx,n} = h_{qx}^H f_n. \quad (16)$$

When $H_{px,n}$ is defined in similar manner, the impedance for frequency $f_n$ is $$z_n = H_{px,n}/H_{qx,n}. \quad (17)$$

When the eigenvalues are put into the diagonal matrix $\Lambda_{qx} \equiv \text{diag}\{H_{qx,0}, \ldots, H_{qx,N-1}\}$ and the corresponding eigenvectors as columns into the N×N matrix $F^H$, Eq. 15 becomes $$C_{qx} F^H = F^H \Lambda_{qx}. \quad (18)$$

Circulants are normal matrices (they commute with their Hermitian transpose). Eq. 18 is therefore in agreement with the spectral theorem, which says that an N×N normal matrix has N orthogonal eigenvectors (in this case, the N orthogonal column vectors $f_n$).

The Uncertainty Principle for Discrete Time and Frequency.

The components of $x \equiv \{x_t\}$ are sharply localized in the time domain, but uncertain in the frequency domain. Conversely, the components of the Fourier transform F x are sharply localized in the frequency domain, but uncertain in the time domain. To obtain a signal with small uncertainty in both domains, a measure of uncertainty has to be defined.

Assuming that time is circular, the approach of Forbes and Alonso seems most appropriate (see reference 3). Referring now to FIG. 3A, in the time domain, the squared components $|x_t|^2$ are placed as point masses at regular intervals on a circle with radius $r_t$ in the complex plane, centered at the origin, with the size of each point mass in FIG. 3A corresponding to the weight of each event. Time is represented by the arc length between two events. The circumference of the circle is the total period N (where N=12 in this illustration), so that the radius equals $r_t \equiv N/(2\pi)$. A given event at time t is located at point $r_t \omega^t$ in the complex plane. Forbes and Alonso (reference 3) proposed several measures of uncertainty. Here a slightly different measure is used, defined as the weighted mean of the squared distances between each event at time t and the event at a reference time $t_R$, $$\Delta_t^2 \equiv \sum_{t=0}^{N-1} |r_t \omega^t - r_t \omega^{t_R}|^2 |x_t|^2 \Big/ \sum_{t=0}^{N-1} |x_t|^2. \quad (19)$$

This measure of uncertainty has the advantage that it can easily be expressed as a ratio of quadratic forms. Without loss of generality, it can be assumed that $t_R = 0$ (as shown in FIG. 3A). Then the squared uncertainty $\Delta_t^2$ is $$\Delta_t^2 = r_t^2 x^H (\Omega - I)^H (\Omega - I) x / \|x\|^2, \quad (20)$$

where the diagonal matrix $\Omega \equiv \text{diag}\{1, \omega^1, \ldots, \omega^{N-1}\}$. It is possible to define $$\Delta_t = r_t \|Ax\|/\|x\|, \quad (21)$$

where $A \equiv \Omega - I$. Physically, $\Delta_t^2$ is the second moment of inertia of the set of point masses about an axis (perpendicular to the plane of the circle) through the reference point R (corresponding to time $t_R$). As depicted in FIG. 3B, this moment of inertia is directly related to the center of gravity. Geometrically, $\Delta_t$ equals the distance from R to one of the two points where the vertical line through the center of gravity intersects with the circle. So, $\Delta_t$ is fully determined by the horizontal distance from the center of gravity to R. If the center of gravity coincides with R, then the weight of x is entirely concentrated at time $t_R$ and $\Delta_t$ is zero. If the center of gravity lies at the opposite point of the circle, then the weight is entirely concentrated at that point and $\Delta_t$ is maximal, equal to $2r_t$. Thus, in FIG. 3B, the vertical line through the center of gravity B crosses the circle at point C. The uncertainty $\Delta_t$ equals the distance $\overline{CR}$.

In the frequency domain, the components of F x are associated with frequencies $f_n = n/N$. The same components would be obtained for frequencies n/N+j, where j is any integer (see Eqs. 9, 10). The components of F x are therefore periodic in the frequency domain, with unit period. A comparable measure of uncertainty can thus be defined in the frequency domain, relative to a reference frequency $f_R$. The squared magnitudes of the components of F x are again placed as point masses on a circle in the complex plane. The radius now equals $r_f \equiv 1/(2\pi)$ so that the circumference equals unity. If $f_R = 0$, then $$\Delta_f = r_f \|(\Omega - I) F x\|/\|x\|. \quad (22)$$

The diagonal matrix $\Omega$ is related to the 'time shift operator' $T \equiv \text{circ}\{0, \ldots, 0, 1\}$. Premultiplication of x by T circularly shifts the components of x one place downward. It readily follows from Eq. 18 that $F T^{-1} = \Omega F$ (the 'shift theorem'), so that $$\Delta_f = r_f \|(\Omega F - F) x\|/\|x\| = r_f \|F(T^{-1} - I) x\|/\|x\|.$$

Since F is unitary, $\|F(T^{-1}-I)x\| = \|(T^{-1}-I)x\|$. Letting $B \equiv T^{-1} - I$, $$\Delta_f = r_f \|Bx\|/\|x\|. \quad (23)$$

Now consider the matrix $$C \equiv r_t \begin{bmatrix} A \\ B \end{bmatrix}.$$

The total uncertainty in time and frequency may be expressed by the ratio $$x^H C^H C x/\|x\|^2 = r_t^2 x^H (A^H A + B^H B) x/\|x\|^2 = \Delta_t^2 + N^2 \Delta_f^2. \quad (24)$$

This ratio (a Rayleigh quotient) can take values in the range from the minimal to the maximal squared singular value of C. This yields the corresponding uncertainty principle for discrete time and frequency, $$\sigma_{min}^2 \le \Delta_t^2 + N^2 \Delta_f^2 \le \sigma_{max}^2. \quad (25)$$

Accordingly, it is impossible that $\Delta_t$ and $\Delta_f$ are both very small, since the total uncertainty $\Delta_t^2 + N^2 \Delta_f^2$ should at least be equal to $\sigma_{min}^2$. The total uncertainty is minimal if x is an eigenvector of $C^H C$ that corresponds to $\Delta_{min}^2$. The eigenvectors of $C^H C$ can be regarded as discrete Mathieu functions. An interesting property of $C^H C$ is that it commutes with F, so that $C^H C$ and F share the same eigenvectors. The eigenvalue of F that corresponds to $v_{min}$ equals unity, so that $F v_{min} = v_{min}$. As is depicted in FIG. 4A, this means that $\Delta_t = N \Delta_f$ if x equals $v_{min}$. FIG. 4 shows the time series for which the sum $\Delta_t^2 + N^2 \Delta_f^2$ is minimal. In FIG. 4A, the eigenvector is derived for reference time $t_R = 0$ and frequency $f_R = 0$ (upper graph). This is also an eigenvector of the Fourier matrix F (with unit eigenvalue), so that the time series remains unchanged after transformation to the discrete frequency domain (lower graph). In these graphs, both of the time and frequency axes are circularly shifted for visual reasons. FIG. 4B corresponds to FIG. 4A but with a reference frequency $f_R = \frac{1}{4}$. In FIG. 4B, closed circles represent real values, open circles represent imaginary values, and crosses indicates the absolute values.

See the section entitled "Derivation of the uncertainty principle" below for a more detailed analysis of the uncertainty principle.

The Discrete Time-Frequency Domain.

The ODFT partitions a time series of N events into a set of oscillations with N different frequencies. A simple way to perform a time-frequency analysis is to compute the ODFT repeatedly for short-lasting sequences of M successive events (with M<N). Accordingly, the series is partitioned into M oscillations with frequencies $f_m \equiv m/M$ (with m=0, ..., M−1), which amounts to a discrete 'short-time Fourier transform'. The resulting uncertainty in time and frequency is minimal if each short-lasting oscillation is 'windowed' with the components of $v_{min}$.

For a sequence of M events, such a windowed oscillation is described by the M-vector $$v_{min}^{(m)} = \Omega^m v_{min}. \quad (26)$$

An example is shown in FIG. 4B. Note that $v_{min}^{(m)}$ is in fact a circularly shifted version of $v_{min}$ in the frequency domain. As is illustrated in FIG. 4 and proven in the "Derivation of the uncertainty principle" section below (see Eq. B19), it has the same uncertainty in time and frequency as the eigenvector $v_{min}$ (if $f_m$ is taken as reference frequency). Let the components of $v_{min}^{(m)}$ be denoted by $v_{min,t}^{(m)}$. An N-vector that describes a short-lasting oscillation is then obtained by inserting zeros in the middle of $v_{min}^{(m)}$ (so that the unimodal structure of the vector remains intact). This gives $$h_{m,0} = \{v_{min,0}^{(m)}, \ldots, v_{min,K}^{(m)}, 0, \ldots, 0, \\ v_{min,K+1}^{(m)}, \ldots, v_{min,M-1}^{(m)}\}/\|v_{min}\|, \quad (27)$$

where K is the smallest integer less than or equal to M/2. This oscillation is centered about time t=0 and frequency $f_m = m/M$. In general, the oscillation in $$h_{m,t} \equiv T^t h_{m,0} \quad (28)$$

is centered about time t and frequency $f_m$.

The best-fitting linear relation between x and $h_{m,t}$ in the least-squares sense follows from the orthogonal projection of x onto the (complex) one-dimensional subspace spanned by $h_{m,t}$. Taking into account that $h_{m,t}$ is defined as a unit vector (see Eq. 27), this projection is $$h_{m,t} h_{m,t}^H x/\|h_{m,t}\|^2 = h_{m,t} h_{m,t}^H x. \quad (29)$$

For a given frequency $f_m$, let the N×N matrix $M_m$ be defined as $$M_m \equiv \text{circ}\{h_{m,0}^H\}. \quad (30)$$

This is a circulant that acts a band-pass filter with resonant frequency $f_m$. Premultiplication of x by $M_m$ gives an N-vector that may be denoted by a tilde or 'wave sign', $$\tilde{x}_m = M_m x. \quad (31)$$

The components of $\tilde{x}_m$ are the inner products $\tilde{x}_{m,t} = h_{m,t}^H x$.

The full time frequency transform (TFT), encompasses all frequencies $f_m$ for m=0, ..., M−1. Let the MN×N matrix M be defined as $$M \equiv \frac{1}{\sqrt{M}} \begin{bmatrix} M_0 \\ \vdots \\ M_{M-1} \end{bmatrix}. \quad (32)$$

Transformation to 'the' discrete time-frequency domain (the time-frequency domain) is performed by premultiplication of x by M (specific for a given M). This gives the MN-vector $\tilde{x} = M x$. Back-transformation means multiplication again, by $M^H$, giving $M^H \tilde{x} = M^H M x$. In the section entitled "Derivation of the time-frequency transform" below, it is shown that the columns of M are orthonormal, so that $$M^H M = I. \quad (33)$$

Back-transformation thus recovers the original time series, since $M^H M x = I x = x$. This makes a time-frequency synthesis of x possible according to $$x = \frac{1}{M} \sum_{m=0}^{M-1} \sum_{t=0}^{N-1} h_{m,t} \tilde{x}_{m,t}. \quad (34)$$

The time series is thus written as the weighted sum of MN short-lasting oscillations, each centered about time t and frequency $f_m$ (cf. Eq. 14). For a given M, these oscillations give an optimal time-frequency resolution according to the uncertainty principle of Eq. 25. As shown in the "Derivation of the uncertainty principle" section below, the oscillations can be approximated by a truncated Gaussian with $M' = 10 \cdot \Delta_t$ nonzero elements.

Input to the Excitation Source.

It is convenient to use a set of harmonic oscillations as excitation source input x. To analyze the data, the scale M of the TFT can then be chosen so that the frequencies of these oscillations coincide with the TFT resonant frequencies $f_m$. First consider a single sinusoidal input with frequency $f_n$ and amplitude $a_m$. Due to Euler's theorem (Eq. 10), a real-valued harmonic oscillation is the sum of a complex-valued oscillation and its complex conjugate. The excitation source input can thus be written $$x = \tfrac{1}{2}(a_m f_n + a_m^* f_n^*), \tag{35}$$

where the asterisk denotes the complex conjugate. From Eqs. 9 and 10, it follows that $f_n^* = f_{N-n}$. The frequency $f_n = n/N$ can be matched with a TFT resonant frequency $f_m \equiv m/M$ if N is an integer multiple of M. If in is subsequently chosen so that $f_n = f_m$, $$\tilde{x}_m = M_m(\tfrac{1}{2} a_m f_n + \tfrac{1}{2} a_m f_{N-n}) \approx \tfrac{1}{2} a_m f_n. \tag{36}$$

The latter approximation is valid if M is large enough and the corresponding $\Delta_f$ small enough to suppress the oscillation at frequency $f_{N-n}$ by the TFT filter with resonant frequency $f_n = f_m$. A full representation of the excitation source input in the time-frequency domain is obtained if the component at the 'complementary frequency' $f_{N-n}$ (here equal to $f_{M-m}$) is also included by adding $M_{M-m}$ to $M_m$ in Eq. 36.

The model of Eq. 8 is transformed to the time-frequency domain by premultiplying both the equations by M. Concentrating on the frequencies of the interest (e.g., the frequency of the forced oscillation described by Eq. 35), multiplying the upper part of Eq. 8 by $M_m$ yields $$M_m Q = M_m \mu_Q + M_m C_{qx} x + M_m Q_e \tag{37}$$

It is readily shown that $M_m \mu_Q$ is zero if $m \neq 0$. Thus, $$\tilde{Q}_m = M_m C_{qx} x + \tilde{Q}_{e,m} \tag{38}$$

Since circulants all commute, it follows that $M_m C_{qx} x = C_{qx} M_m x = C_{qx} \tilde{x}_m$. If n and m are chosen so that $f_n = f_m$, then, using Eqs. 36 and 15, $$C_{qx} \tilde{x}_m = \tfrac{1}{2} a_m C_{qx} f_n = \tfrac{1}{2} a_m f_n H_{qx,n} = \tilde{x}_m H_{qx,n} \tag{39}$$

When $H_{qx,n}$ for $f_n = f_m$ is denoted by $b_{Q,m}$ (and the corresponding $H_{px,n}$ by $b_{P,m}$), the model of Eq. 8 reduces to $$\begin{cases} \tilde{Q}_m = \tilde{x}_m b_{Q,m} + \tilde{Q}_{e,m} \\ \tilde{P}_m = \tilde{x}_m b_{P,m} + \tilde{P}_{e,m} \end{cases} \tag{40}$$

The impedance for $f_n = f_m$ is $$z_m \equiv b_{P,m} / b_{Q,m} \tag{41}$$

A set of other oscillations can be added to the excitation source input of Eq. 35, provided that $\Delta_f$ of the used TFT is small enough so that these oscillations are well separated in the time-frequency domain.

Analysis of Variance in the Time-Frequency Domain.

The TFT permits an analysis of variance in the time-frequency domain (see the section below entitled "Analysis of variance in the time-frequency domain"). For instance, the squared norm of the noise in flow (see Eq. 8) can be partitioned into $$\|Q_e\|^2 = \frac{1}{M} \sum_{m=0}^{M-1} \|\tilde{Q}_{e,m}\|^2 \tag{42}$$

The random variable $\|\tilde{Q}_{e,m}\|^2/N$ may be called the 'TFT sample power spectrum' of the noise $Q_e$. Suppose that the transfer function of filter 1 from noise 1 to $Q_{e,t}$ (FIG. 2) is relatively flat in the passband of the TFT filter about $f_m$. Then $\tilde{Q}_{e,m}$ is approximately distributed as if it were derived from white noise with zero mean and variance $\sigma_{Q,m}^2 I$. As a result, $\|\tilde{Q}_{e,m}\|^2/\sigma_{Q,m}^2$ follows an approximate chi-square distribution with equivalent degrees of freedom $\eta$. See section "Analysis of variance in the time-frequency domain" below for a derivation of $\eta$, where only those components of $\tilde{Q}_{e,m}$ are included that are independent of the circularity assumption (as well as the component at the complementary frequency $f_{M-m}$).

Bivariate Least Squares in the Time-Frequency Domain.

It is now assumed that at every time t, a new temporarily stationary process starts that is described by the model of FIG. 2. The process encompasses N events and is assumed to be circular (that is, periodic in N). In the time-frequency domain, the model becomes (from Eq. 40)

$$\begin{cases} \tilde{Q}_{t,m} = \tilde{x}_{t,m} b_{Q,t,m} + \tilde{Q}_{e,t,m} \\ \tilde{P}_{t,m} = \tilde{x}_{t,m} b_{P,t,m} + \tilde{P}_{e,t,m} \end{cases} \tag{43}$$

where the vectors are 'short-lasting' N-vectors now, starting at time t. Note that the constants $b_{Q,m}$ and $b_{P,m}$ have acquired the index t as well, since they are assumed to be specific for the time at which the process starts. The constants, as well as the inputs to the model, may therefore be different at different times t (even if two processes overlap in time).

Figure 5:
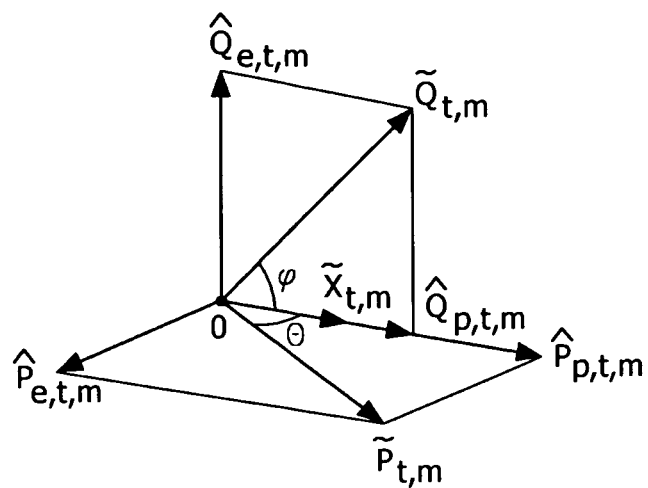
FIG. 5 illustrates the bivariate least squares in the time-frequency domain.

The best-fitting estimators of $b_{Q,t,m}$ and $b_{P,t,m}$ can be derived from $\tilde{x}_{t,m}$, $\tilde{Q}_{t,m}$ and $\tilde{P}_{t,m}$ by minimizing the squared norm of the error vectors. This yields the least-squares estimators $\hat{B}_{Q,t,m}$ and $\hat{B}_{P,t,m}$. The estimated relations are $$\begin{cases} \tilde{Q}_{t,m} = \tilde{x}_{t,m} \hat{B}_{Q,t,m} + \hat{Q}_{e,t,m} \\ \tilde{P}_{t,m} = \tilde{x}_{t,m} \hat{B}_{P,t,m} + \hat{P}_{e,t,m} \end{cases}, \tag{44}$$

where the estimated 'predicted' vector $\hat{Q}_{p,t,m} \equiv \tilde{x}_{t,m} \hat{B}_{Q,t,m}$ is orthogonal to the estimated 'error' $\hat{Q}_{e,t,m}$ (and, similarly, $\hat{P}_{p,t,m}$ is orthogonal to $\hat{P}_{e,t,m}$). In FIG. 5, the vectors are depicted as arrows and all variables refer to time index t and frequency index m (corresponding to frequency $f_m = m/M$). In particular, in FIG. 5, the excitation source input $\tilde{x}_{t,m}$ is a fixed variable, while the flow $\tilde{Q}_{t,m}$ and pressure $\tilde{P}_{t,m}$ are random variables. The vectors $\hat{Q}_{p,t,m}$ and $\hat{P}_{p,t,m}$ are the projections of $\tilde{Q}_{t,m}$ and $\tilde{P}_{t,m}$ onto the complex one-dimensional subspace spanned by $\tilde{x}_{t,m}$ (the line l). The impedance estimator follows from $\hat{P}_{p,t,m} = \hat{Q}_{p,t,m} \hat{Z}_{t,m}$. The error vectors $\hat{Q}_{e,t,m}$ and $\hat{P}_{e,t,m}$ are perpendicular to $\tilde{x}_{t,m}$. Each vector is represented by an arrow whose length equals the norm. The angles between the vectors are drawn so that $\cos^2 \phi$ and $\cos^2 \theta$ equal the squared coherences between $\tilde{x}_{t,m}$ and, respectively, $\tilde{Q}_{t,m}$ and $\tilde{P}_{t,m}$.

The degree of linear relation between $\tilde{x}_{t,m}$ and $\tilde{Q}_{t,m}$ comes to expression in the 'TFT squared sample coherence'

$$K_{Qx,t,m}^2 \equiv \frac{|\tilde{x}_{t,m}^H \tilde{Q}_{t,m}|^2}{\|\tilde{x}_{t,m}\|^2 \|\tilde{Q}_{t,m}\|^2} \tag{45}$$

The random variable $\tilde{x}_{t,m}{}^H \tilde{Q}_{t,m}/N$ may be called the 'TFT sample cross spectrum' from x to Q. Geometrically, $K_{Qx,t,m}{}^2$ equals $\cos^2\phi$, where $\phi$ is the angle from $\tilde{x}_{t,m}$ to $\tilde{Q}_{t,m}$ in FIG. 5. Similarly, $K_{Px,t,m}{}^2$ equals $\cos^2\theta$. The least-squares estimators are derived in the standard way. This gives $$\hat{B}_{Q,t,m} = \tilde{x}_{t,m}{}^H \tilde{Q}_{t,m}/\|\tilde{x}_{t,m}\|^2 \tag{46}$$

Accordingly, $\hat{B}_{Q,t,m}$ is the ratio of the sample cross spectrum from x to Q to the sample power spectrum of x. When $\hat{B}_{P,t,m}$ is derived in a similar way, the impedance is estimated by $$\hat{Z}_{t,m} = \hat{B}_{P,t,m}/\hat{B}_{Q,t,m} \tag{47}$$

The 'true' impedance $z_{t,m}$ has a real part $r_{t,m}$ ('resistance') and imaginary part $x_{t,m}$ ('reactance'). The corresponding estimators are the real and imaginary parts of $\hat{Z}_{t,m}$, $$\hat{Z}_{t,m} = \hat{R}_{t,m} + i\hat{X}_{t,m} \tag{48}$$

Figure 6A:
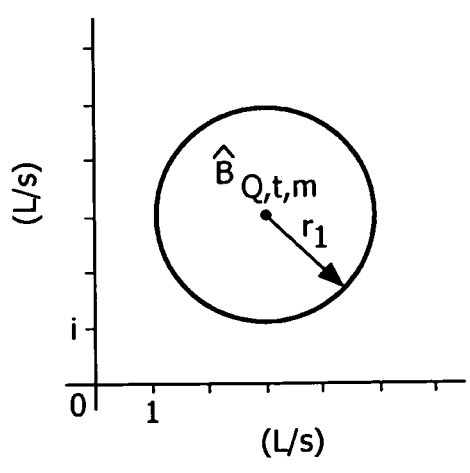
FIG. 6 illustrates confidence region in the complex plane.

As is depicted in FIG. 6A, the 100(1−α)% confidence region for $b_{Q,t,m}$ is delimited by a circle in the complex plane, centered about $\hat{B}_{Q,t,m}$. The confidence region is given by $$|b_{Q,t,m} - \hat{B}_{Q,t,m}|^2 \leq |\hat{B}_{Q,t,m}|^2 A_{Q,t,m}{}^2, \tag{49}$$

where $A_{Q,t,m}{}^2 \equiv F_\alpha \cdot 2(1 - K_{Qx,t,m}{}^2)/(\eta-2)K_{Qx,t,m}{}^2$ and $F_\alpha$ is the upper 100(1−α)% point of the F-distribution (see the section entitled "Derivation of confidence limit" below). The excitation source input $x_t$ is a dimensionless variable so $\hat{B}_{Q,t,m}$ has units of flow (since $\hat{Q}_{p,t,m} = \tilde{x}_{t,m} \hat{B}_{Q,t,m}$ from FIG. 5). The values that depend on the circularity assumption are discarded here (the effective number of samples is $N_S = N - M + 1$). The relation will be rejected if the origin is within the circle (then $\hat{B}_{Q,t,m}$ is not significantly different from zero at the 100·α% confidence level). Hence, it follows from Eq. 49 that significance is obtained if $A_{Q,t,m} < 1$. The confidence region for $\hat{B}_{P,t,m}$ is delimited by a comparable circle and the relation between $\tilde{x}_{t,m}$ and $\tilde{P}_{t,m}$ is considered significant if $A_{P,t,m} < 1$.

A conservative estimate of the confidence region for $\hat{Z}_{t,m}$ is derived in the section entitled "Derivation of confidence limits" below, under the assumption that $\tilde{Q}_{e,t,m}$ and $\tilde{P}_{e,t,m}$ are uncorrelated. The region is described by $$\left| z_{t,m} - \hat{Z}_{t,m} \frac{1 + A_{Q,t,m} A_{P,t,m}}{1 - A_{Q,t,m}^2} \right|^2 \leq \left| \hat{Z}_{t,m} \frac{A_{Q,t,m} + A_{P,t,m}}{1 - A_{Q,t,m}^2} \right|^2 \tag{50}$$

Figure 6B:
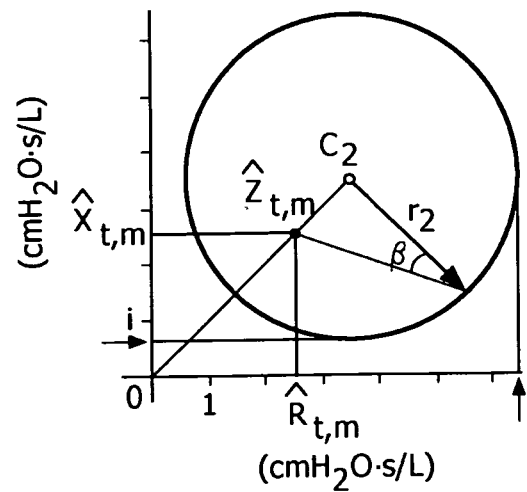

Referring to FIG. 6B, the limiting circle is not concentric about the estimator $\hat{Z}_{t,m}$. The real and imaginary parts of $\hat{Z}_{t,m}$ are represented by $\hat{R}_{t,m}$ and $\hat{X}_{t,m}$. The vertical arrow indicates the upper confidence limit for the real part and the horizontal arrow indicates the lower confidence limit for the imaginary part of the impedance. The distribution of 'true' $z_{t,m}$ for a given realization of $\hat{Z}_{t,m}$ is apparently skew-symmetric. In FIG. 6B, the skewness is determined by the angle β. The skewness is entirely due to the noise in flow, as appears from the relation between β and the angle φ in FIG. 5, $$\tan^2\beta = A_{Q,t,m}{}^2 = \tan^2\phi \cdot F_\alpha \cdot 2/(\eta-2) \tag{51}$$

If the noise in flow is zero, then $\phi=0$, $K_{Qx,t,m}{}^2=1$ and $A_{Q,t,m}=0$, so that $\beta=0$ and the confidence region is symmetric about $\hat{Z}_{t,m}$.

The section entitled "Derivation of confidence limits" below gives a further analysis of what happens if it is assumed that either the noise in flow or the noise in pressure is zero. The respective estimators would then be equal to $$\hat{Z}_{t,m}{}^{(Q)} = \tilde{Q}_{t,m}{}^H \tilde{P}_{t,m}/\|\tilde{Q}_{t,m}\|^2 \text{ and } \hat{Z}_{t,m}{}^{(P)} = \|\tilde{P}_{t,m}\|^2/\tilde{P}_{t,m}{}^H \tilde{Q}_{t,m} \tag{52}$$

This amounts to linear regression from flow to pressure (or conversely) in the time-frequency domain. The variables $\|\tilde{Q}_{t,m}\|^2/N$, $\|\tilde{P}_{t,m}\|^2/N$ and $\tilde{Q}_{t,m}{}^H \tilde{P}_{t,m}/N$ are the respective sample power and cross spectra. The main difference between the estimators of Eq. 52 and $\hat{Z}_{t,m}$ lies in the magnitude of the estimated impedance. The magnitudes are related through $$|\hat{Z}_{t,m}{}^{(Q)}/K_{Qx,t,m}{}^2 = |\hat{Z}_{t,m}| = |\hat{Z}_{t,m}{}^{(P)}|K_{Px,t,m}{}^2 \tag{53}$$

It follows that, if noise is present in both flow and pressure, the magnitude of impedance is underestimated if $\hat{Z}_{t,m}{}^{(Q)}$ is used instead of $\hat{Z}_{t,m}$ (and overestimated if $\hat{Z}_{t,m}{}^{(P)}$ is used).

Settings.

In use of the apparatus 2, flow and pressure were recorded at a sample rate of 800 Hz. A TFT was performed with $\Delta_t = 50$ (which amounts to 50/800=0.0625 s). This would require a width of the TFT filter of $M = 4\pi\Delta_t{}^2 = 31,416$. However, the coefficients of the TFT filter were approximated by a Gaussian truncated at $M' = 10 \cdot \Delta_t = 500$ (see the "Derivation of the uncertainty principle" section below). The associated uncertainty in frequency is $\Delta_f = 1/(4\pi\Delta_t) = 0.0016$ (or 0.0016× 800=1.27 Hz). The TFT was derived for $f_m = 0.01, 0.015, 0.02, 0.025, 0.03$, corresponding to the imposed FOT frequencies of 8, 12, 16, 20, 24 Hz. Sample power and cross spectra were computed for $N_S = 500$ (that is, over a time interval of 500/800=0.625 s). Only data were used that are independent of the circularity assumption. This leads to an approximate chi-square distribution of the sample spectra with η=6.72. Confidence limits for impedance were derived for the 90% confidence level ($F_\alpha = 4.05$). Time-frequency spectra were aligned in time with the original time series.

EXAMPLES

Figure 7:
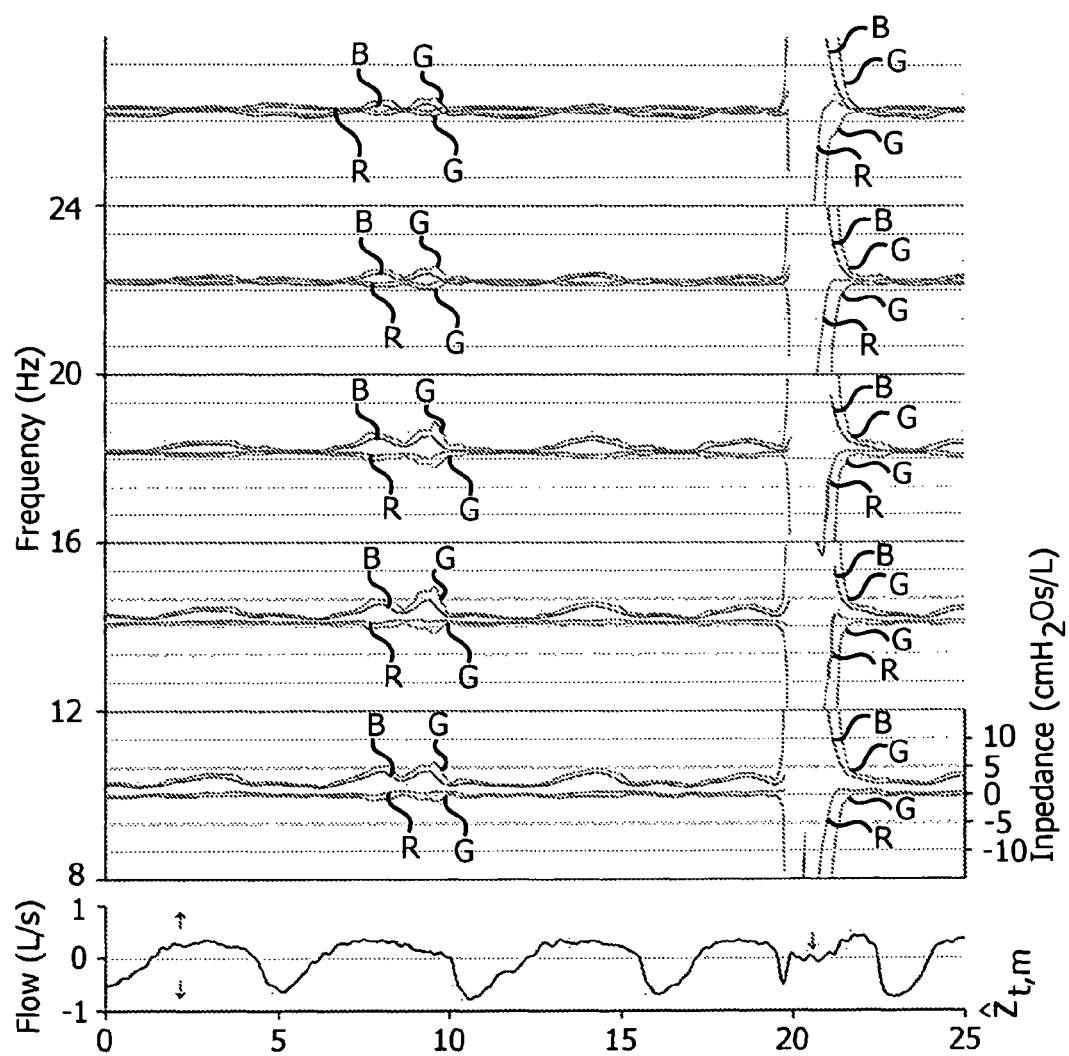
FIG. 7 illustrates the respiratory impedance in a healthy patient as a function of time and frequency with confidence limits for forced pressure oscillations at five different frequencies.

FIG. 7 shows the real and imaginary parts of the estimated impedance $\hat{Z}_{t,m}$ as a function of time and frequency for a normal subject. The blue lines represent the real part $\hat{R}_{t,m}$ and the red lines represent the imaginary part $\hat{X}_{t,m}$. The grey lines represent the confidence limits as depicted in FIG. 6B. The right hand axis of the 8 Hz frequency band indicates the scale of the components of impedance. At 8 Hz, the real part $\hat{R}_{t,m}$ is positive and fluctuates in the course of the respiratory cycle, while the imaginary part $\hat{X}_{t,m}$ is almost equal to zero and remains relatively constant. The confidence limits give an immediate impression of the statistical significance of the changes in $\hat{R}_{t,m}$ and $\hat{X}_{t,m}$ in the course of time. At higher frequencies, $\hat{R}_{t,m}$ decreases while $\hat{X}_{t,m}$ gradually becomes more positive. The signals were severely disturbed when the subject swallowed on request, which was accompanied by a large increase in the confidence region. The associated coherence spectra are shown in section "Derivation of confidence limits" below.

Figure 8:
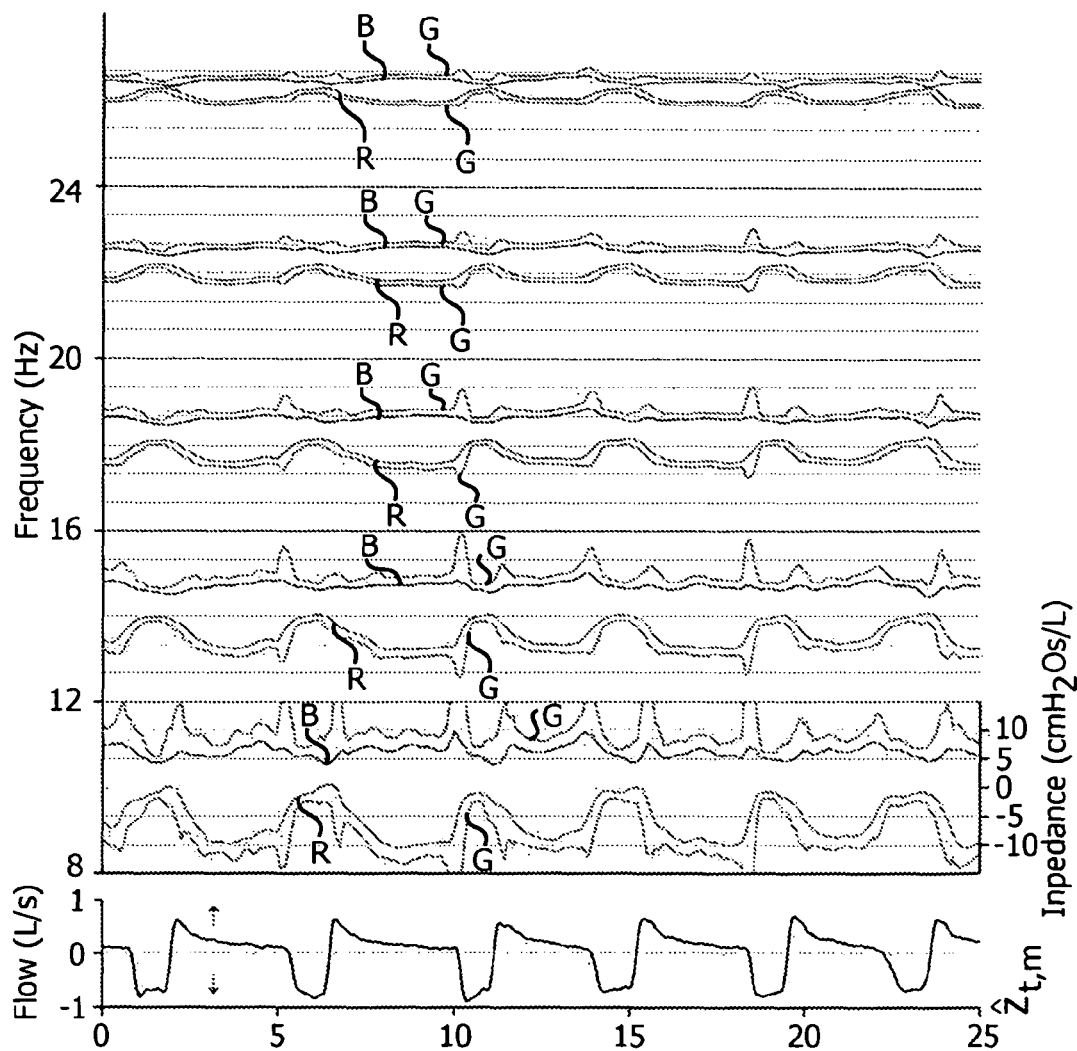
FIG. 8 illustrates the respiratory impedance in a patient with COPD as a function of time and frequency with confidence limits for forced pressure oscillations at five different frequencies.

FIG. 8 shows the impedance for a patient with COPD with large negative swings in $\hat{X}_{t,m}$ during expiration (which are obviously significantly different from the inspiratory values in view of the confidence limits). Such negative swings have previously been described in COPD and are related to flow limitation due to submaximal collapse of the airways during expiration. The confidence region is maximal at the turning points from inspiration to expiration and vice versa, probably due to the high-frequency content of the patient's own breathing, which disturbs the forced oscillations. See section "Derivation of confidence limits" below for the coherence spectra.

Discussion

Figure 9:
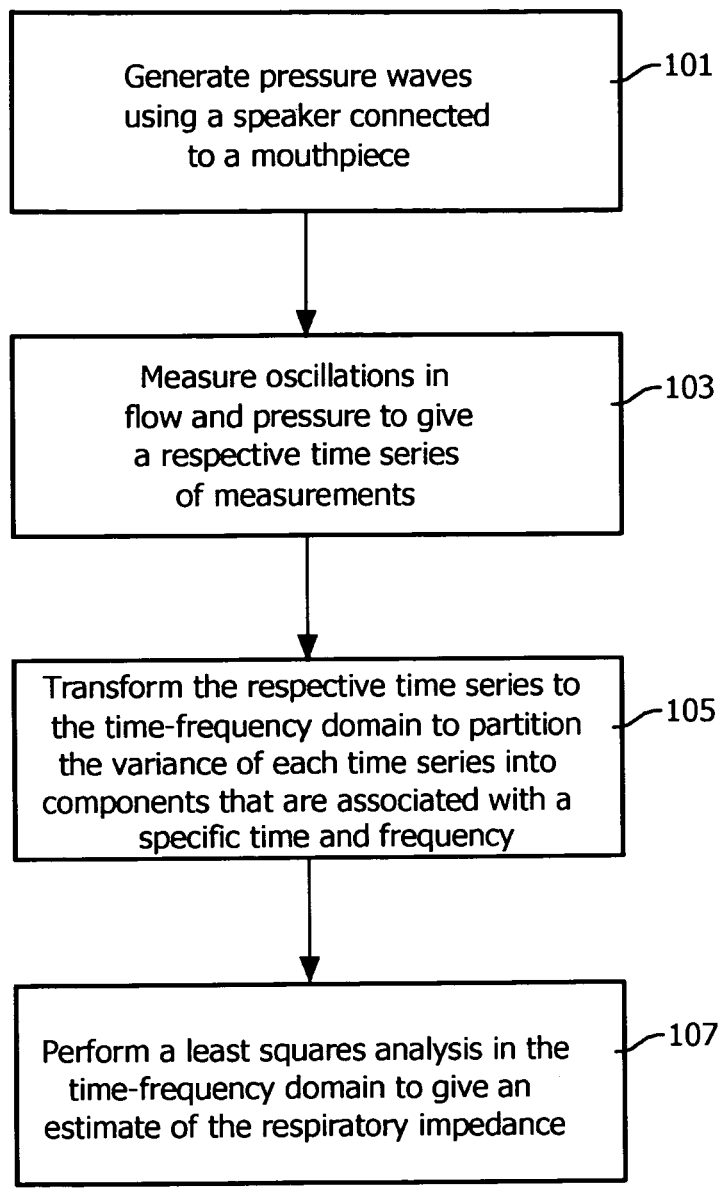
FIG. 9 is a flow chart illustrating the steps in the method of estimating the respiratory impedance in accordance with the invention.

FIG. 9 is a flow chart that summarizes the steps in the method according to the invention. In this exemplary embodiment, pressure waves are generated using a loudspeaker connected to a mouthpiece as a patient interface device 4 that is in communication with an airway of a subject (step 101). The oscillations in flow and pressure of the gas passing through the mouthpiece 4 are measured to give a respective time series of measurements (step 103). In the steady state, the respiratory impedance can be inferred from forced pressure oscillations in the mouthpiece 4 of a quietly breathing subject. Since the mechanical properties of the respiratory system often change from inspiration to expiration, the method estimates the impedance under circumstances of temporary 'stability'. The main problem is that impedance is a frequency-dependent quantity and that a high time resolution inevitably leads to a low frequency resolution, thereby distorting the estimation. Since the data consists of discrete time series (sequential measurements of flow and pressure in the mouthpiece 4), this asks for an optimal time-frequency analysis of short time series.

As described in the "Methods" section above, the present invention is based on the concept that a short time series can be stationary if time is assumed to be circular (see below). As described, a new version of the uncertainty principle has been derived for such time series, which poses a lower limit to the total uncertainty in the time and frequency domain. In step 105, this principle is used to partition the variance of each time series into components that are associated with a specific time and frequency (through transformation to the 'discrete time-frequency domain' or 'time-frequency domain'). Least squares analysis in the time-frequency domain then gives an unbiased estimator of impedance with optimal time-frequency resolution (step 107). Finally, confidence limits for impedance have been constructed as a function of time and frequency. The main steps are summarized and discussed below.

The Linear Model.

The estimation of respiratory impedance is based on a simple linear model (Eq. 3, FIG. 2). Oscillations in the mouthpiece 4 of the apparatus 2 are induced by a loudspeaker 6. The resulting changes in flow and pressure depend on the mechanical properties of the patient's respiratory system (the acoustics of that system). In the model, this is expressed by two linear time-invariant filters (2 and 3 in FIG. 2) that modify the loudspeaker input. The resulting fluctuations in flow and pressure are disturbed by two independent sources of noise in both flow and pressure. The respiratory impedance is determined by the two linear filters (2 and 3).

Possible sources of noise are: 1) components of the patient's breathing in the frequency range of the forced oscillations, which is probably the most important problem (see reference 2), 2) swallowing, coughing or other movements by the patient, 3) cardiogenic oscillations, in particular when the airway resistance is low, 4) time-dependent variations in respiratory impedance itself and 5) random measurement errors.

A linear model has been used previously to explain the frequency-dependent relation between flow and pressure during similar experiments (see reference 2), although there have been indications that nonlinear interactions in the respiratory system are not negligible. A linear description of the relation between flow and pressure in the FOT device 2 is however supported by the fact that the pressure differences are small compared to the mean absolute pressure. Using an impedance to describe the relation is a simplification of the interaction of standing waves that can be expected under these circumstances. The main restriction, however, seems to lie in the time during which the respiratory system can be considered as stable.

The Circularity Assumption.

To account for chance events, it has been assumed that flow and pressure are random variables (RVs) with a given probability distribution. A short sequence of N paired measurements of flow and pressure is thus considered as a sample from a finite bivariate stochastic process (a set of N chronologically ordered paired RVs). The frequency-dependent relation between flow and pressure in such a process can only be described by a stable impedance if the bivariate stochastic process is assumed to be (second-order) stationary. This means that the expected values of flow and pressure are constant, as well as the covariances between simultaneous and successive values. The covariances between successive values cannot be constant for a finite sequence, however, due to begin- and end-effects (unless these covariances are equal to zero).

However, this problem is solved by assuming that time is circular, in the sense that the last event precedes the first. In this way, the covariances between successive values may be constant, while the sequence still consists of a finite number of RVs. This is a direct consequence of the discrete and finite nature of the sequence. Think of a clock, at which it is only possible to look at the whole hours (a chronological sequence of N=12 events). If you look at one o'clock (time $t_1$) and at two o'clock (time $t_2$), it is possible that one hour has elapsed from $t_1$ to $t_2$, but it is also possible that 13 hours have passed or that the event at $t_2$ took place 11 hours before $t_1$. Without further knowledge, it is not possible to discern between a time difference of one hour and one hour plus or minus an integer multiple of 12. This indeterminacy is directly related to 'aliasing' (which happens if ones tries to reconstruct a continuous signal from such a time series). Still, accidental changes in the last part of the measured sequence may cause fluctuations in both variables that do not continue in the first part. This would cause a bias in the estimation of impedance, which is however ruled out in the applied time-frequency analysis (see below).

The Uncertainty Principle.

'Uncertainty in time' is a property of a time series that expresses how much the components of the series are spread in time. For a discrete, finite and circular time series, this gives a figure as shown in FIG. 3A. The components of the time series are represented by point masses placed at regular intervals around the time circle (each mass equals the squared absolute value of a component). The uncertainty $\Delta_t$ is defined with respect to a reference point (here the point where t=0, Eq. 19) and is closely related to the center of gravity (Eq. B3). If the time series has only one nonzero component (at time t=0), then the center of gravity is located at t=0 and $\Delta_t$ is zero. If all components have equal weight, then the center of gravity is located at the center and $\Delta_t$ is high (associated with maximal spread in the time domain).

Similarly, the 'uncertainty in frequency' $\Delta_f$ expresses the spread in the frequency domain (Eq. 22). Through the discrete Fourier transform, every time series with N components can be written as the sum of N harmonic oscillations with a given amplitude and frequency (representation in the discrete frequency domain). For a discrete time series, these frequencies are also circular. The spread in the frequency domain can be visualized by placing the squared amplitudes as N point masses around a circle comparable to that in FIG. 3A (each point corresponding to a specific frequency).

For continuous time and frequency, it has been shown that there is a trade-off between uncertainty in time and frequency, expressed by the uncertainty relation $$\Delta_t \Delta_f \geq 1/(4\pi) \qquad (54)$$

This holds for continuous and infinite time series (under certain conditions). If $\Delta_t$ is small, $\Delta_f$ has to be large since the product should at least be equal to $1/(4\pi)$, and vice versa. This inequality is directly related to Heisenberg's famous uncertainty principle for position and momentum of a particle. For discrete time series, however, the lower limit of the product $\Delta_t \Delta_f$ is zero (see also "Derivation of the uncertainty principle" below). Still, there is a restriction on joint values of $\Delta_t$ and $\Delta_f$. In the "Methods" section above (Eq. 25), it is shown that for discrete, finite and circular time series, $$\Delta_t^2 + N^2 \Delta_f^2 \geq \sigma_{min}^2 \qquad (55)$$

where $\sigma_{min}$ is a function of N. Thus, $\Delta_t$ and $\Delta_f$ cannot be both very small. The sum $\Delta_t^2 + N^2 \Delta_f^2$ is minimal for a time series whose discrete Fourier transform is exactly equal to the original time series (FIG. 4A). As N gets large, this time series with minimal joint uncertainty in time and frequency approaches a Gaussian function of time. This time series is analogous to the minimal uncertainty state of two attracting particles in quantum mechanics (the so-called 'quantum harmonic oscillator'). Forbes et al. (see reference 4) derived a similar time series from the wave equation for such an oscillator. In the present case, however, this minimal uncertainty state is simply derived from the definitions of $\Delta_t$ and $\Delta_f$ for discrete and finite time series. In "Derivation of the uncertainty principle" below, it is shown how the uncertainty principle of Eq. 55 relates to Gabor's uncertainty principle for large N (see FIG. 14).

The Discrete Time-Frequency Domain.

The presented time-frequency transform (TFT) partitions a discrete and finite time series into a set of short-lasting oscillations of M components, with M<N (a transformation to the time-frequency domain). Each oscillation is centered about a specific time and frequency, with minimal uncertainty in both domains according to the principle of Eq. 55. The TFT amounts to a windowed 'short-term Fourier transform' or 'running Fourier transform'. The short-lasting oscillations maximally overlap each other in time so that the outcome is independent of the time at which the first oscillation starts. Only the oscillations that start before the beginning and end after the end of the time series are dependent on the circularity assumption (these are excluded in the analysis to avoid bias). In the "Derivation of the time-frequency transform" section below, it is shown that the transform is 'orthonormal' (Eq. 33), which implies that all information in the time series is preserved after transformation to the discrete time-frequency domain. Nothing is gained, nothing is lost. An inverse-transformation recovers the original time series.

To be precise, it is not possible to refer to 'the' discrete time-frequency domain, but only about the time-frequency domain for a chosen value of M. This integer determines the duration of each short-term oscillation, but it also equals the number of different frequencies about which these oscillations are centered (the TFT resonant frequencies). As shown in "Derivation of the uncertainty principle" below, the optimal $\Delta_t$ and $\Delta_f$ according to the uncertainty principle of Eq. 55 depends on M (substitute N by M in Eq. B8, see also FIG. 11). Not surprisingly, the larger M, the larger the corresponding optimal $\Delta_t$ and the smaller the corresponding $\Delta_f$. In the present analysis, M is chosen so that $\Delta_f$ is small enough to be able to discern the different oscillations induced by the loudspeaker.

Input to the Loudspeaker.

In an exemplary embodiment, a set of five harmonic oscillations we used as an input to the loudspeaker 6 (at frequencies of 8, 12, 16, 20 and 24 Hz respectively). For the analysis, the value of M (actually an effective value, see Eq. B6) was chosen so that the uncertainties were, expressed in time units, $\Delta_t$=0.0625 s and $\Delta_f$=1.27 Hz. The TFT coefficients were only computed for these five frequencies, which amounts to band-pass filtering with five resonant frequencies. One prior art approach uses a single frequency for the loudspeaker input. This poses less requirements to the time-frequency analysis (they used a band-pass filter with rectangular window, with a larger $\Delta_f$ for a given $\Delta_t$ than in the present invention). For a single frequency, the frequency resolution is less critical, although it may still be useful to filter out the higher harmonics of the patient's breathing. On the other hand, the frequency dependence of impedance can provide additional information on respiratory mechanics. Alternatively, broad-band noise can be applied, which has the disadvantage that the power of the input signal is gradually distributed over all frequencies, with relatively less power at the studied frequencies (a lower signal-to-noise ratio at the same total power of the loudspeaker). In yet another approach, a ventilator waveform was applied that was built up of nonharmonic sinusoids to ventilated patients to prevent interaction between oscillations at harmonic frequencies. Such an approach is however not applicable in freely breathing subjects. Some interference of the respiratory system at harmonic frequencies may indeed occur in the present invention, although this has not been observed in the frequency response of the system after broad-band stimulation.

Analysis of Variance in the Time Frequency Domain.

The orthonormal property of the TFT makes it possible to partition the variance of a stochastic process into time-frequency dependent components, which gives the time-frequency power spectrum (see "Analysis of variance in the time-frequency domain" below). The TFT sample power expresses the contribution of a short-lasting oscillation about a given time and frequency to the total sample variance. Analysis of the TFT power spectrum thus amounts to an analysis of variance in the time-frequency domain (Eq. 42). In the model (Eq. 43), it is assumed that there are independent sources of noise in flow and pressure, together forming a bivariate circularly stationary stochastic process. When the values that depend on the circularity assumption are discarded, a number of $N_S$=500 successive values in the time-frequency domain are considered as a sample from this process (an episode of 0.625 s at a sample rate of 800 Hz). It was assumed that at every moment (800 times per second) a new stochastic process of this type starts with a variance that is not necessarily equal to the previous one. Thus, the measurements were subdivided into maximally overlapping episodes of 500 values, each of which was considered as a sample from a different stationary stochastic process. The sources of noise were not assumed to be 'white', but it was assumed that the power was constant in each frequency band of the TFT filter. The mean power during each episode of 500 values then follows an approximate chi-square distribution for which the equivalent degrees of freedom were derived.

Bivariate Least Squares in the Time-Frequency Domain.

For each episode of $N_S=500$ successive values, the coefficients of the linear relation between loudspeaker input and flow ($b_{Q,t,m}$) and the relation between input and pressure ($b_{P,t,m}$) were estimated by simple linear regression in the time-frequency domain (Eq. 44, FIG. 5). This results in unbiased estimators associated with time t and frequency $f_m$ (respectively, $\hat{B}_{Q,t,m}$ and $\hat{B}_{P,t,m}$, see Eq. 46). Each estimator is based on time-averaged power and cross spectra over $N_S$ values in the time-frequency domain. Subsequently, the impedance was estimated by the ratio $\hat{Z}_{t,m}=\hat{B}_{P,t,m}/\hat{B}_{Q,t,m}$.

The choice of N depends on the time during which the system can be considered as stationary. For respiration, an episode of ~0.5 s seems plausible, assuming that the impedance is approximately stable in the midst of each inspiration and expiration. In the shown examples, this worked out well (FIGS. 7 and 8). In most prior art techniques, however, spectra are averaged over a longer episode, usually of more than 10 s. Some averaged spectral values derived from non-overlapping segments of ~0.65 s over a total episode of 16 s. The use of non-overlapping segments, however, gives considerably less degrees of freedom for an episode of the same length as compared to the maximally overlapping segments used here (i.e., the segments of M values used in the TFT). The major problem is that the use of an episode of 16 s averages out possible physiological differences between inspiration and expiration, which are usually more pronounced in diseases such as COPD. In that case, a low coherence between flow and pressure over 16 s is not only a reflection of noise, but also of within-breath variability of impedance (which is part of the disease). The duration of the supposed stationary should not be chosen too short, either. In the example of FIG. 8, the confidence intervals for are relatively wide at the turning points from inspiration to expiration and vice versa. This may be due to high-frequency components of the patient's own breathing. These changes are apparently shorter than 0.5 s, so that they appear as noise in the estimation. The duration of the supposed stationary should therefore be long enough to 'interpret' these changes as noise.

Since the impedance estimator $\hat{Z}_{t,m}$ is derived as the ratio of two normally distributed RVs ($\hat{B}_{P,t,m}$ and $\hat{B}_{Q,t,m}$), it follows a Cauchy distribution which has no expected value. So, strictly speaking, $\hat{Z}_{t,m}$ has no bias in the sense of a difference between expected and true value. Still, since $\hat{B}_{P,t,m}$ and $\hat{B}_{Q,t,m}$ are unbiased normally distributed RVs, $\hat{Z}_{t,m}$ is by approximation normally distributed with expectation $z_{t,m}=b_{P,t,m}/b_{Q,t,m}$. Daróczy and Hantos (reference 2) followed a similar approach, deriving the impedance estimator as the ratio of the regression coefficients from the loudspeaker input to respectively flow and pressure. Based on a simple model of the mechanical properties of patient and apparatus, they argued that a systematic error is introduced if it is assumed that noise only occurs in either flow or pressure. Experimental evidence for such bias has been found. Others, however, assumed that the loudspeaker generates a pressure wave and the main noise, the high-frequency component of the patient's own breathing, is a pure flow source (while the noise in pressure is zero). If the TFT would have been used, the estimator would be $\hat{Z}_{t,m}^{(P)}$ in Eq. 52. On the other hand, other documents used an estimator analogous to $\hat{Z}_{t,m}^{(Q)}$ in Eq. 52. Since $\hat{Z}_{t,m}^{(P)}$ and $\hat{Z}_{t,m}^{(Q)}$ are least-squares estimators under the assumption that the noise in either pressure or flow is zero, this leads to bias if this is not in agreement with reality, which was already pointed out by several authors (see reference 2). It has been argued that this type of error is minimal if the coherence between flow and pressure is high and recommended to discard the estimates for which this is not the case. This is in line with Eq. 53, from which it follows that $\hat{Z}_{t,m}^{(P)}$ and $\hat{Z}_{t,m}^{(Q)}$ both approach $\hat{Z}_{t,m}$ (and thus the true $z_{t,m}$) if the coherence tends to unity. The discussion surrounding Eqs. 50 and 51 also shows that the noise in flow also affects the confidence region for impedance (in particular the skewness parameter tan β, see FIG. 6B). In one earlier document, band-pass filtered pressure was divided by flow to obtain impedance as a function of time (see above). The resulting impedance is numerically equal to a 'total least squares' estimate with equivalent contributions of the sample variances in flow and pressure. It can be expected that these values are often in the same range as those obtained with bivariate least squares (if the coherence from input to flow equals the coherence from input to pressure). This 'estimator' is however not derived from averaged values which makes it highly susceptible to random error.

Thus far, confidence limits on the estimated impedance have only been derived for relatively time long intervals. The time-frequency dependent confidence limits in embodiments of the present invention provide a continuous impression of the validity of the hypothesis that the short-lasting sequences are samples from a stationary stochastic process. They make it possible to test the significance of changes in impedance in the course of time and provide a basis to automatically reject unreliable estimates (like during swallowing in FIG. 7), which is of practical interest in real-time monitoring.

Figure 10:
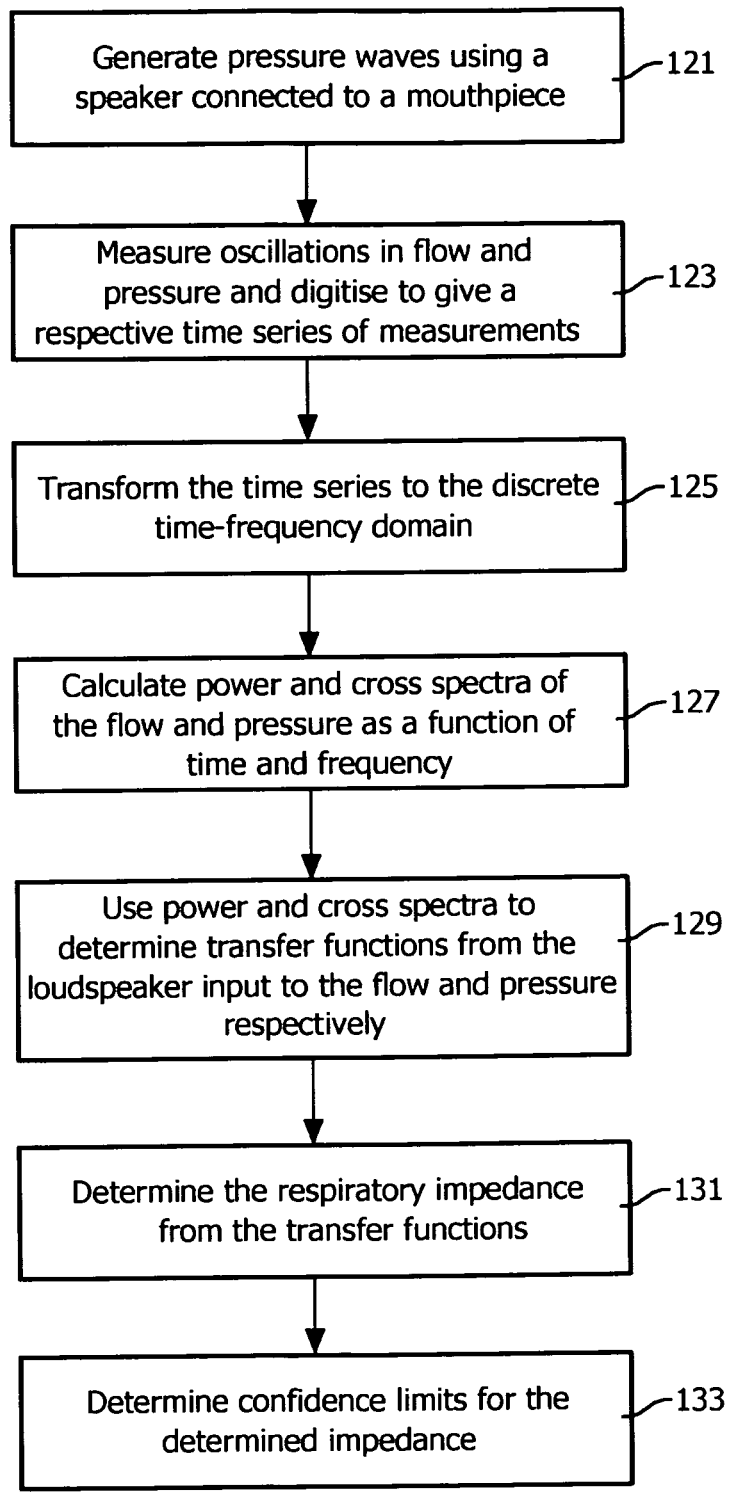
FIG. 10 is a flow chart illustrating the processing steps performed by the apparatus according to the invention in more detail.

FIG. 10 is a flow chart illustrating the method performed by the apparatus 2 according to the invention (and particularly the processing steps performed by the computer 16) in more detail. As in FIG. 9, in step 121, pressure waves are generated using a loudspeaker 6 connected to a mouthpiece 4 that is being used by a subject, and the oscillations in flow and pressure of the air passing through the mouthpiece 4 are measured and digitized to give a respective time series of measurements (step 123). Thus flow and pressure are given as a function of discrete time t, $q_t$ and $p_t$.

Then, in step 125, the time series are each transformed into the discrete time-frequency domain to give flow $\tilde{q}_{t,m}$ and pressure $\tilde{p}_{t,m}$ as a function of discrete time t and different frequencies $f_m=m/M$, where in is the frequency index and M is the effective width of the time-frequency filter. The frequencies $f_m$ are chosen so that they match the frequencies of the imposed FOT frequencies.

Step 125 comprises evaluating:

$$\tilde{q}_{t,m} = \sum_{l=-K_1}^{K_1} \omega_l e^{-2\pi i m l/M} q_{t+l}, \tag{56}$$

for the flow time series $q_t$ where $i^2=-1$ and the weighting factor $w_l$ is approximated by a Gaussian function of time, $w_l = e^{-(l/\Delta_t)^2}$ and $\Delta_t$ is the chosen uncertainty in time. The filter is truncated at $K_1=5\cdot\Delta_t$. While the weighting factor $w_l$ is described here as being approximated by a Gaussian function, it is to be understood that other windows or weighting factors are contemplated by the present invention, such as a triangle window, a piece-wise linear approximation, or a polynomial function.

The pressure $\tilde{p}_{t,m}$ as a function of time and frequency is derived analogously from $$\tilde{p}_{t,m} = \sum_{l=-K_1}^{K_1} w_l e^{-2\pi i m l/M} p_{t+l} \qquad (56a)$$

Then, in step 127, the power and cross spectra are derived as a function of time and frequency. The power of the flow is given by:

$$P_{q,t,m} = \frac{1}{N_S} \sum_{l=-K_2}^{K_2} |\tilde{q}_{t+l,m}|^2, \qquad (57)$$

where $N_S$ is the number of samples in the time-frequency domain, $K_2 = \frac{1}{2}(N_S-1)$ if $N_S$ is odd and $|\cdot|$ stands for the absolute value.

The power of the pressure, represented by $P_{p,t,m}$ is derived analogously from $$P_{p,t,m} = \frac{1}{N_S} \sum_{l=-K_2}^{K_2} |\tilde{p}_{t+l,m}|^2 \qquad (57a)$$

The cross spectrum from the loudspeaker input $\tilde{x}_{t,m}$ to the flow $\tilde{q}_{t,m}$ in the time-frequency domain is given by:

$$C_{xq,t,m} = \frac{1}{N_S} \sum_{l=-K_2}^{K_2} \tilde{x}^*_{t,m} \tilde{q}_{t,m}, \qquad (58)$$

where the asterisk denotes the complex conjugate.

The cross spectrum from loudspeaker input to pressure, $C_{xp,t,m}$, is derived from $\tilde{x}_{t,m}$ and $\tilde{p}_{t,m}$ in a similar way:

$$C_{xp,t,m} = \frac{1}{N_S} \sum_{l=-K_2}^{K_2} \tilde{x}^*_{t,m} \tilde{p}_{t,m} \qquad (58a)$$

In step 129, the power and cross spectra are used to determine the transfer functions from the loudspeaker input to flow and pressure respectively.

In particular, the transfer function from loudspeaker input to flow is given by the ratio of the cross spectra to the power:

$$B_{xq,t,m} = \frac{C_{xq,t,m}}{P_{x,t,m}}, \qquad (59)$$

and the transfer function from loudspeaker input to pressure, $B_{xp,t,m}$, is derived analogously:

$$B_{xp,t,m} = \frac{C_{xp,t,m}}{P_{x,t,m}} \qquad (59a)$$

Thus, in step 131, the impedance of the respiratory system can be determined from the ratio of the transfer functions:

$$Zrs_{t,m} = \frac{B_{xp,t,m}}{B_{xq,t,m}}, \qquad (60)$$

with real component $Rrs_{t,m}$ and imaginary component $Xrs_{t,m}$.

Furthermore, confidence limits on the respiratory impedance can be derived (step 133) as follows.

The equivalent number of degrees of freedom $\eta$ of the power and cross spectra is given by:

$$\eta = \frac{(tr\{P^H P\})^2}{tr\{(P^H P)^2\}}, \qquad (61)$$

where P is an N×N matrix, H stands for the Hermitian transpose and $tr\{\cdot\}$ for the trace of the matrix. The matrix P is defined as $$P = S(M_m + M_{M-m})/N_S. \qquad (62)$$

where S is a diagonal matrix S that has $N_S$ ones on the main diagonal (and the rest zeros), i.e.

$$S = \text{diag}\{0, \ldots, 0, 1, \ldots, 1, 0, \ldots, 0\}. \qquad (63)$$

The (shifted) time-frequency transform matrix $M_m$ is a circulant whose entries on the first row are $w_l e^{2\pi i \, ml/M}$, for $l = -K_3, \ldots, K_3$ and $K_3 = \frac{1}{2}(N-1)$ where N is odd. $F_\alpha$ is labeled as the upper $100(1-\alpha)$ % point of the F-distribution on $2, \eta-2$ degrees of freedom.

The squared coherence between $\tilde{x}_{t,m}$ and $\tilde{q}_{t,m}$ is given by:

$$K^2_{xq,t,m} = \frac{|C_{xq,t,m}|^2}{P_{x,t,m} \cdot P_{q,t,m}}, \qquad (64)$$

and the squared coherence between $\tilde{x}_{t,m}$ and $\tilde{p}_{t,m}$, $K^2_{xp,t,m}$, is derived analogously from $$K^2_{xp,t,m} = \frac{|C_{xp,t,m}|^2}{P_{x,t,m} \cdot P_{p,t,m}} \qquad (64a)$$

The flow-related variable $A_{q,t,m}^2$ is defined as $$A^2_{q,t,m} = F_\alpha \left(\frac{2}{\eta-2}\right)\left(\frac{1-K^2_{xq,t,m}}{K^2_{xq,t,m}}\right), \qquad (65)$$

and the analogous pressure-related variable, denoted $A_{p,t,m}^2$, is derived in a similar way from $$A^2_{p,t,m} = F_\alpha \left(\frac{2}{\eta-2}\right)\left(\frac{1-K^2_{xp,t,m}}{K^2_{xp,t,m}}\right) \qquad (65a)$$

Therefore, the $100(1-\alpha)$ % confidence limits for the real and imaginary parts of the respiratory impedance are given by, respectively, $$Rrs \cdot c_1 \pm c_2 \text{ and } Xrs \cdot c_1 \pm c_2,$$

with $c_1 = 1 + A_{q,t,m} \cdot c_3, c_2 = |Zrs_{t,m}| \cdot c_3$, and $$c_3 = \frac{A_{q,t,m} + A_{p,t,m}}{1 - A_{q,t,m}^2}.$$

The estimates of respiratory impedance for a given time and frequency are rejected as not significant if either $A_{q,t,m} \geq$ a first threshold, or $A_{p,t,m} \geq$ a second threshold. In an exemplary embodiment, the first threshold and the second threshold are set to 1 (one), so that the estimates of respiratory impedance for a given time and frequency are rejected as not significant if either $A_{q,t,m} \geq 1$ or $A_{p,t,m} \geq 1$.

To deal with begin- and end-effects, the algorithm contains several circular data buffers.

The Measurement Apparatus

Measurements.

The airflow can be measured with a pneumotach head 8 and built-in pressure transducer 10 (for example a Jaeger Masterscreen pneumotach type BF/IEC 601-1, Hoechberg, Germany). The pressure at the mouthpiece 4 can be measured with reference to ambient air with a differential pressure transducer 12 (for example a Hans Rudolph Pneumotach amplifier 1 series 1110, Shawnee, Kans.). The pressure oscillations can be generated in the FOT device 2 by a loudspeaker 6 (for example a Jaeger Masterscreen IOS, Hoechberg, Germany) that is controlled by an analog output signal from a personal computer 16 (for example a Hewlett Packard Compac dc 7600, Palo Alto, Calif.) through an analog-digital conversion card 14 (for example a National Instruments PCI-6221, Dallas, Tex.), which is amplified by an amplifier 18 (for example a Harman Kardon HK 970 amplifier, Washington D.C.)). Subjects can breathe in and out through the mesh-wired resistance 9 connected to the pneumotach head 8. Analog input signals can be converted to digital sequences through the same analog-digital conversion card 14 at a sample rate of 800 Hz and stored in the personal computer 16. The generation of the output signal and the analysis of the data can be performed by a computer or processor 16 executing appropriate computer software.

Measurements can be made using the apparatus 2 during a period covering a number of breathing cycles, for example 90 seconds of quiet breathing.

Derivation of the Uncertainty Principle

Geometrical Interpretation of Uncertainty in Time and Frequency.

According to the definition of Eq. 20, the uncertainty $\Delta_t$ is directly related to the 'center of gravity' of the time series $x \equiv \{x_t\}$. The events in the time series are represented as point masses with value $|x_t|^2$, placed at regular intervals around the perimeter of a circle with radius $r_t$ in the complex plane, centered about the origin. Each event occurs at a point $r_t \omega^t$ in the complex plane, with $r_t \equiv N/(2\pi)$ and $\omega \equiv \exp(2\pi i/N)$. The weighted mean $\bar{\omega}_t$ can be defined as $$\bar{\omega}_t \equiv \sum_{t=0}^{N-1} \omega^t |x_t|^2 \Big/ \sum_{t=0}^{N-1} |x_t|^2 \quad (B1)$$

The center of gravity is located at $r_t \bar{\omega}_t$. In matrix formulation, $$\bar{\omega}_t = x^H \Omega x / \|x\|^2, \quad (B2)$$

where $\Omega \equiv \text{diag}\{1, \omega, \ldots, \omega^{N-1}\}$. Using the fact that $\Omega$ is a unitary matrix, the squared uncertainty $\Delta_t^2$ can then be reduced to $$\Delta_t^2 \equiv r_t^2 x^H (\Omega - I)^H (\Omega - I) x / \|x\|^2 \quad (B3)$$
$$= r_t^2 x^H (\Omega^H \Omega + I - \Omega^H - \Omega) x / \|x\|^2$$
$$= r_t^2 x^H \left[ 2I - 2 \cdot \frac{1}{2}(\Omega^H + \Omega) \right] x / \|x\|^2$$
$$= 2 r_t^2 (1 - \text{Re}\{\bar{\omega}_t\}).$$

Figure 12:
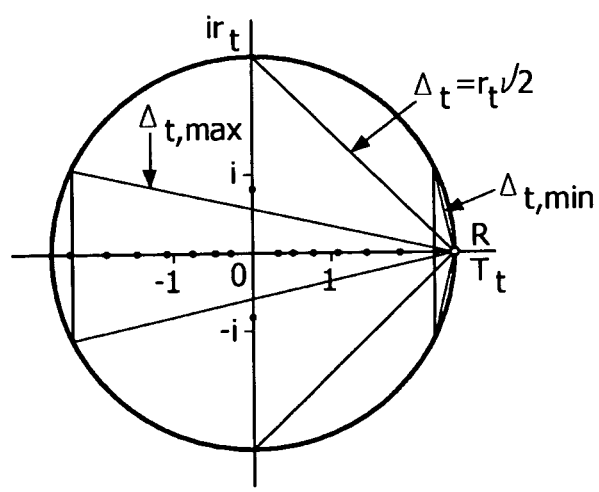
FIG. 12 illustrates the relation between uncertainty in time $\Delta_t$ and the centers of gravity of the eigenvectors of $C^H C$ for N=16.

This is in line with the 'parallel axes theorem' for the second moment of inertia about an axis (perpendicular to the plane of the circle) through the reference point R in FIG. 12. FIG. 12 illustrates the relation between uncertainty in time $\Delta_t$ and the centers of gravity of the eigenvectors of $C^H C$ for N=16. The eigenvectors are mapped along the time circle in the complex plane with radius $r_t$, centered about the origin. The centers of gravity of each eigenvector are depicted by black dots. The corresponding singular value of C is minimal for the center of gravity at the right (near to the reference point R) and gradually increases to the left of the Figure. The uncertainty $\Delta_t$ for each eigenvector is the oblique distance from R to one of the intersection points of the vertical line through the center of gravity and the circle.

Figure 13:
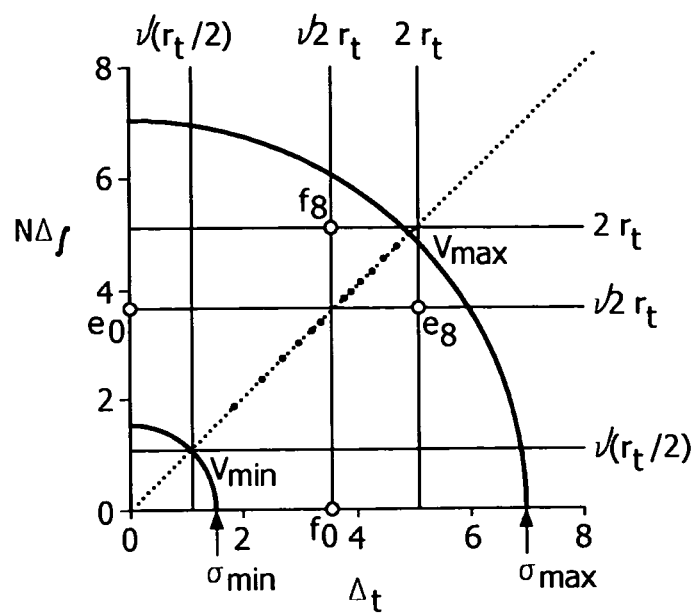
FIG. 13 illustrates the relation between uncertainty in time $\Delta_t$ and uncertainty in frequency $\Delta_f$ for N=16.

In the representation of FIG. 13, it follows from Eq. 11 that $\Delta_t^2 = 2r_t \cdot \overline{AR}$, where $\overline{AR}$ is the distance from A to R in FIG. 12. Using the Pythagorean theorem, it follows that $\Delta_t = \overline{CR}$, since $$\overline{CR}^2 = \overline{AC}^2 + \overline{AR}^2 = r_t^2 - (r_t - \overline{AR})^2 + \overline{AR}^2 = 2 r_t \cdot \overline{AR}$$

In the frequency domain, the uncertainty $\Delta_f$ can be geometrically interpreted in a similar manner.

Singular Values of the Matrix C.

Figure 11:
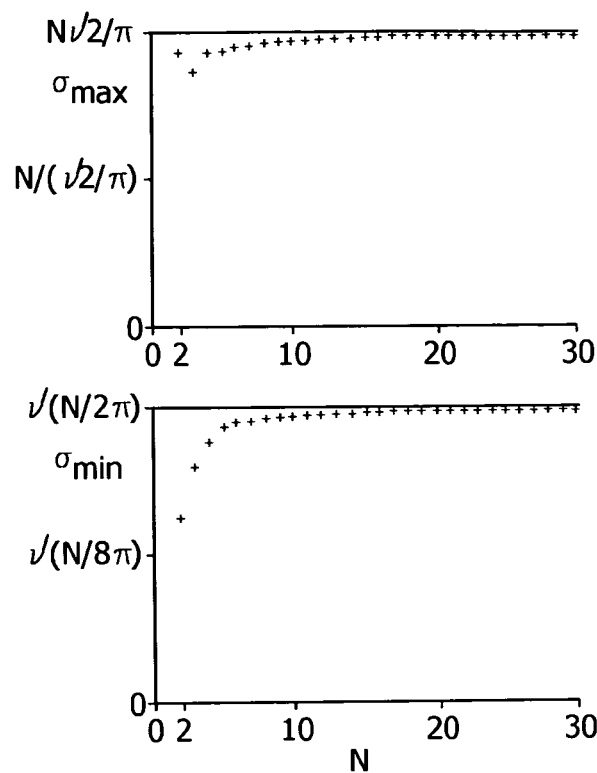
FIG. 11 shows the minimal and maximal singular values of the matrix C as a function of the number of events N in a time series.

The uncertainty principle of Eq. 25 is determined by $\sigma_{min}^2$ and $\sigma_{max}^2$, the squared minimal and maximal singular values of C. The singular values $\sigma$ can be derived from $$\det(C^H C - \sigma^2 I) = 0 \quad (B4)$$

where det(•) stands for the determinant of the matrix. For N=2, it readily follows that $\sigma_{min}^2 = 2(2-\sqrt{2})/\pi^2$ and $\sigma_{max}^2 = 2(2+\sqrt{2})/\pi^2$. For higher N, various strategies have been developed to derive the singular values of C (the eigenvalues of $C^H C$). FIG. 11 shows $\sigma_{min}$ and $\sigma_{max}$ as a function of N. It turns out that for larger N (say, N>15), $\sigma_{min}$ approaches $\sqrt{N/2\pi}$ and $\sigma_{max}$ approaches $N\sqrt{2}/\pi$. In terms of the radius of the time circle, this means that $\sigma_{min} \approx \sqrt{r_t}$ and $\sigma_{max} \approx 2\sqrt{2} r_t$.

Let v be a unit eigenvector of $C^H C$ that corresponds to singular value $\sigma$. The normal equations $(C^H C - \sigma^2 I) v = 0$ can be rewritten as $$r_t^2 [(\Omega - I)^H (\Omega - I) + (T^{-1} - I)^H (T^{-1} - I)] v - \sigma^2 v = \quad (B5)$$
$$r_t^2 [\Omega^H \Omega + I - \Omega^H - \Omega + TT^{-1} + I - T - T^{-1}] v -$$
$$\sigma^2 v = [r_t^2 (2I - \Omega^H - \Omega) - \sigma^2] v - r_t^2 (T - 2I + T^{-1}) v = 0.$$

The first term depends on the departure of the components of v from the reference point R along the real axis (cf Eq. B3). The second term can be seen as the second derivative of the components of v (for discrete and circular time). Equation B5 is comparable to the Schrödinger equation for a quantum harmonic oscillator. The solutions can be regarded as discrete orthogonal Mathieu functions. The eigenvector $v_{min}$ that corresponds to $\sigma_{min}$ is a unimodal function of time (as in FIG. 4A). For large N, $v_{min}$ can be approximated by a vector $v_{min}'$, whose components $v_{min,t}'$ are a Gaussian function of time, $$v_{min,t}' = v_{min,0}' \exp[-(t/2\Delta_t)^2] \quad (B6)$$

where N has to be subtracted from t if $t \geq \frac{1}{2}N$. Since the components $v_{min,t}'$ are close to zero if $t > 5 \cdot \Delta_t$, the Gaussian can be truncated by using only the $10 \cdot \Delta_t$ largest values about the maximal value and setting the rest to zero. Calling the resulting approximated eigenvector $v'$, and the difference vector $d \equiv v - v'$, the norm $\|d\|$ can be taken as a measure for the error made by the approximation. Using appropriate mathematical software, it follows that the relative error $\|d\|/\|v\|$ is less than 0.005 if N>75.

Since $C^H C$ commutes with F, these matrices share the same eigenvectors. Since $F^4 = I$, the eigenvalues of F are 1, −1, i and −i. As a result, for every unit eigenvector v, the uncertainty in time is directly related to the uncertainty in frequency, $$\Delta_t = r_t \|(\Omega - I)v\| = N/2\pi \|(\Omega - I)Fv\| = N\Delta_f \quad (B7)$$

This means that for every eigenvector v, the total uncertainty is evenly distributed over time and frequency, $$\sigma^2 = v^H C^H C v = \Delta_t^2 + N^2 \Delta_f^2 = 2\Delta_t^2 = 2N^2 \Delta_f^2 \quad (B8)$$

So, for every eigenvector v, $\Delta_t = N\Delta_f = \sigma/\sqrt{2}$. Note that the Gaussian approximation of $v_{min}$ according to Eq. B6 can be rewritten as $v_{min,t}' = v_{min,0}' \exp[-\frac{1}{2}(t/\sigma_{min})^2]$. The total uncertainty $\sigma_{min}^2$ is therefore equal to the variance of this Gaussian function. Equation B8 also implies that, for N>15, the values of $\Delta_t$ that correspond to minimal and maximal total uncertainty are, respectively, $\Delta_{t,min} = \sigma_{min}/\sqrt{2} \approx \sqrt{r_t/2}$ and $\Delta_{t,max} \approx \sigma_{max}/\sqrt{2} \approx 2r_t$. The latter is intuitively reasonable since $2r_t$ is the largest possible $\Delta_t$ within the time circle (see FIG. 13). FIG. 13 illustrates the relation between uncertainty in time $\Delta_t$ and uncertainty in frequency $\Delta_f$ for N=16. The accessible region for all possible N-vectors x is bounded by the two circles with radius $\sigma_{min}$ and $\sigma_{max}$ (the minimal and maximal singular value of C). In FIG. 13, $r_t$ is the radius of the time circle, the black dots belong to the eigenvectors of $C^H C$, $v_{min}$ and $v_{max}$ are eigenvectors corresponding to $\sigma_{min}$ and $\sigma_{max}$, $e_0$ and $e_8$ are canonical vectors corresponding to $t=0$ and $t=8$, $f_0$ and $f_8$ are harmonic oscillations with frequencies $f_n = 0$ and $f_n = 8/16 = \frac{1}{2}$.

As described above, FIG. 12 shows the centers of gravity for all eigenvectors v in the time circle for N=16. Since $C^H C$ is a normal matrix, it has N orthogonal eigenvectors according to the spectral theorem. As appears from Eq. B3, the corresponding $\Delta_t$ depends on the horizontal distance from R to the center of gravity in the complex plane. It can be read from FIG. 12 as the length of the chord from R to the intersection of the circle with the vertical line through the center of gravity. The center of gravity closest to R corresponds to $\sigma_{min}$. Centers of gravity that lie further away correspond to increasing values of $\sigma$ (and $\Delta_t = \sigma/\sqrt{2}$). For relatively large N, the distance between the center of gravity of $v_{min}$ and R approaches $\frac{1}{4}$ which follows from Eq. B3 and the finding that $\Delta_{t,min}$ approaches $\sqrt{r_t/2}$. There is a multiplicity of eigenvalues of $C^H C$ in the sense that there are two orthogonal eigenvectors with the same eigenvalue $\sigma^2 = N^2/\pi^2$. Such multiplicity of eigenvalues probably only occurs if N is divisible by four. The centers of gravity of these two orthogonal eigenvectors are both located on the imaginary axis. They have the same $\Delta_t$, equal to $\sigma/\sqrt{2} = N/(\sqrt{2}\pi) = \sqrt{2}r_t$. The corresponding $\Delta_f$ equals $\Delta_t/N = 1/(\sqrt{2}\pi) = \sqrt{2}r_f$. These two eigenvectors have the largest possible spread in both time and frequency domain (identical to the values that would be obtained if the center of gravity would be located at the center of both the time and frequency circle). Eigenvectors corresponding to higher values of $\sigma$ are associated with larger 'uncertainty' $\Delta_t$ (relative to R), but with a smaller spread in time. The weight of the vectors actually becomes more and more concentrated at the opposite side of both time and frequency circle, until the maximal total uncertainty $\sigma_{max}^2$ is reached for eigenvector $v_{max}$ and $\Delta_t$ is almost equal to $2r_t$. Note the apparent symmetry in FIG. 12 (the centers of gravity are reflected in the imaginary axis).

FIG. 13 shows $N\Delta_f$ as a function of $\Delta_t$. Due to the uncertainty principle of Eq. 25, the accessible region is bounded by two circles centered about the origin, with radius $\sigma_{min}$ and $\sigma_{max}$. This does not mean that all values between these circles are possible, but that all values outside the circles are impossible. The coordinates that belong to the eigenvectors of $C^H C$ are all located on the identity line (due to Eq. B7). Some extreme cases are also shown. One is the canonical vector $e_0 \equiv \{1, 0, \ldots, 0\}$. Its 'weight' $\|x\|^2 = |x_0|^2 + \ldots + |x_{N-1}|^2$ is entirely concentrated at $t=0$, so $\Delta_t$ is zero. Transformation to the frequency domain gives $$F e_0 = \frac{1}{\sqrt{N}} [f_0^* \cdots f_{N-1}^*] e_0 = \frac{1}{\sqrt{N}} f_0^* = \frac{1}{\sqrt{N}} 1 \quad (B9)$$

where $f_n$ is defined as in Eq. 9, the '*' sign stands for the complex conjugate and 1 is the N-vector that contains only ones. Thus, the weight of $e_0$ is evenly distributed over all frequencies in the frequency domain and $\Delta_f = \sqrt{2}r_f$ or $N\Delta_f = \sqrt{2}r_t$. Another extreme is $e_8$. (Let the canonical vector $e_t$ be defined as $\{0, \ldots, 0, 1, 0, \ldots, 0\}$, where the one stands on the tth place, starting from zero.) The weight of $e_8$ is entirely concentrated at the point $(-r_t, 0)$ in the complex plane and so $\Delta_t$ is maximal, equal to $2r_t$. In the frequency domain, $$F e_8 = \frac{1}{\sqrt{N}} [f_0^* \cdots f_{N-1}^*] e_8 = \frac{1}{\sqrt{N}} f_8^* \quad (B10)$$

The column vector $f_8^*$ describes a harmonic oscillation with frequency $f_n = 8/16 = \frac{1}{2}$. Its squared components are also evenly distributed over all frequencies, so $N\Delta_f = \sqrt{2}r_t$. Starting from the time domain, other extremes are the oscillations $f_0$, whose weight is evenly distributed in the time domain and sharply concentrated in the frequency domain at $f_n = 0$ ($\Delta_t = \sqrt{2}r_t$ and $\Delta_f = 0$), and $f_8$, whose weight is also evenly distributed in the time domain but sharply concentrated in the frequency domain at $f_n = \frac{1}{2}$ (so that $\Delta_t = \sqrt{2}r_t$ and $N\Delta_f = 2r_t$). Since possible values for $\Delta_t$ and $N\Delta_f$ are confined to the range $[0, 2r_t]$, it can be expected that all possible combinations $(\Delta_t, N\Delta_f)$ are confined to a region in FIG. 13 that is enclosed by the coordinates for $v_{min}$, $e_0$, $f_8$, $v_{max}$, $e_8$ and $f_0$. These extreme vectors are also illustrations of the general rule: taking the Fourier transform of a time series vector x (through premultiplication by F) exchanges the $(\Delta_t, N\Delta_f)$ coordinates in the plot of FIG. 13. Differently put: the coordinates for x and F x are reflected in the identity line. This is readily verified using the definitions of Eqs. 21 and 23.

Comparison with Gabor's Uncertainty Principle.

The uncertainty principle that was described by Gabor in 1946 (see reference 5 below) determines a lower limit for the product $\Delta_t \Delta_f$ for continuous time and frequency, $$\Delta_t \Delta_f \geq \frac{1}{4\pi} \qquad (B11)$$

How does this inequality relate to the uncertainty principle for discrete time and frequency according to Eq. 25? In Eq. B11, $\Delta_t^2$ is also defined as the second moment of inertia about an axis perpendicular to the point where t=0, although time is mapped on an infinite line now (or a circle with infinite radius). In the derivation of Eq. B11, it is assumed that the mean time is zero (the center of gravity is located at t=0). The same holds for the spread in the frequency domain (regardless of the fact that frequency is not discrete and periodic but continuous and infinite).

The main difference between the inequalities of Eq. B11 and Eq. 25 lies in the fact that according to Gabon's uncertainty principle, the lower limit of $\Delta_t \Delta_f$ is attained for Gaussian functions of t (of the same form as in Eq. B6) with any nonzero value of $\Delta_t$ (see reference 5). This is a set of linearly independent (infinite) vectors. The lower limit of the total uncertainty $\Delta_t^2 + N\Delta_f^2$ according to Eq. 25, however, is attained for only one eigenspace of $C^H C$ (the complex one-dimensional subspace spanned by $v_{min}$), which corresponds to one single value of $\Delta_t$ (equal to $\sigma_{min}/\sqrt{2}$). On the other hand, the vectors in this eigenspace do attain the lower limit of Gabor's uncertainty principle (in the limit situation as N→∞). For every eigenvector of $C^H C$, it follows from Eq. B8 that $$\Delta_t \Delta_f = \Delta_t^2/N = \sigma^2/(2N) \qquad (B12)$$

For $v_{min}$ (or any other vector in the corresponding eigenspace), a approaches $\sqrt{N/(2\pi)}$ as N gets large (FIG. 11). Numerical approximation then shows that, as N→∞, $$\Delta_{t,min} \Delta_{f,min} \uparrow \frac{N}{2\pi} \cdot \frac{1}{2N} = \frac{1}{4\pi} \qquad (B13)$$

For finite N however, $1/(4\pi)$ is not the absolute lower limit for $\Delta_t \Delta_f$. The product is zero for $e_0$ and $f_0$ and addition of small random numbers shows that it is close to zero for slightly different vectors.

The relation between the two uncertainty principles becomes more obvious if we consider the N-vectors that are derived from $v_{min}$ vectors that were obtained for shorter time series (consisting of M events, with 1<M≤N). See the example of FIG. 14, where $v_{min}$ was derived from the 8×8 matrix $C^H C$. The components of F $v_{min}$ are shown as a function of frequency $f_n$ (black dots). These frequencies are multiples of ⅛. Insert a block of 8 zeros between the two smallest components of the 8-vector $v_{min}$ (so that the unimodal structure of the vector remains intact on a circular time base), which results in the 16-vector $$\{v_{min,0}, v_{min,1}, \ldots, v_{min,4}, 0, \ldots, 0, v_{min,5}, \ldots, v_{min,8}\} \qquad (B14)$$

Figure 14:
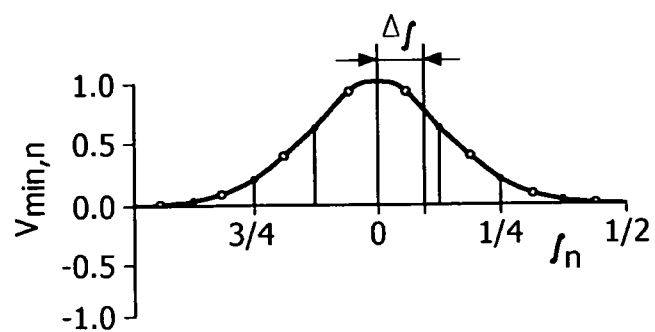
FIG. 14 is a graph plotting $v_{min,n}$ against $f_n$.

This gives a slight increase in $\Delta_t$ (from 0.7583 to 0.7900) and an almost insignificant increase in $\Delta_f$ (from 0.0948 to 0.0949). The open circles in FIG. 14 represent interpolated values in the frequency domain when the block of eight zeros is inserted between the two smallest values of the eigenvector in the time domain, the continuous line represents interpolated values as the number of added zeros in the time domain tends to infinity. The resulting 16-vector leads to interpolation in the frequency domain, at frequencies that are multiples of 1/16 (open circles). This is a well-known form of interpolation in the frequency domain (through 'zero-padding' in the time domain).

In this way, for a given N, a number of N−1 vectors can be derived by adding zeros to smaller M-dimensional $v_{min}$ vectors that are obtained from M×M matrices $C^H C$. A trivial example is $e_0$ that is derived by adding zeros to the '1-vector' $v_{min}$=1 for M=1. FIG. 15 shows the corresponding uncertainties in the plot of $N\Delta_f$ vs. $\Delta_t$ for N=16. These values appear in zone I, delimited by the lines $\Delta_t$=0, $\Delta_t=\sqrt{r_t/2}$, $N\Delta_f=\sqrt{r_t/2}$ and $N\Delta_f=\sqrt{2}\cdot r_t$. The value for M=1 coincides with $e_0$, the value for M=2 is indicated by an arrow and values for higher M gradually approach the value for M=N=16, located at the identity line (which corresponds to $v_{min}$ for N=16). For relatively large M, $\Delta_t$ and $\Delta_f$ are hardly changed by the addition of zeros, while the associated σ approaches $\sqrt{M/(2\pi)}$ so that $$\Delta_t \cdot N\Delta_f \approx \sqrt{\frac{M}{4\pi}} \cdot N \cdot \frac{1}{M} \sqrt{\frac{M}{4\pi}} = \frac{N}{4\pi} \qquad (B15)$$

As a result, the values for relatively large M are plotted slightly below the hyperbola $x \cdot y = N/(4\pi)$ in FIG. 15. As time proceeds and N gets larger, a trail of values grows along this hyperbola, with new values appearing at the identity line. If $\Delta_f$ is plotted against $\Delta_t$, the related hyperbola is given by $x \cdot y = 1/(4\pi)$ and contains all possible values corresponding to different Gaussians at the lower limit of Gabor's uncertainty principle.

Without formal mathematical proof, one may imagine that the N-vectors derived from $v_{min}$ for M<N pose a further limit to the accessible region in the $(\Delta_t, N\Delta_f)$-plane of FIG. 15. Since these vectors have the minimally possible total uncertainty for a sequence of M nonzero events, it can be expected that values outside the region marked by the black dots in FIG. 15 will not occur. This also holds for the values in zone II, which were derived by premultiplying the vectors in zone I by $\Omega^8$, which circularly shifts the vectors in the frequency domain (to the opposite part of the frequency circle), without a change of the weights in the time domain. Thus, $\Delta_f$ of these vectors is maximized without a change in $\Delta_t$. Conversely, the points in zone VI are obtained from the vectors in zone I, premultiplied by $T^8$, which circularly shifts the vectors in the time domain (thereby maximizing $\Delta_t$ without a change in $\Delta_f$). The vectors in zone V follow from those in zone II through premultiplication by $T^8$. The vectors in zone VIII follow from those in zone I by taking the Fourier transform (premultiplication by F means reflection in the identity line). Premultiplying these vectors by $\Omega^8$ gives the vectors in zone III, premultiplying by $T^8$ gives the vectors in zone VII, and premultiplying the latter again by $\Omega^8$ gives those in zone IV. (It will be clear that there are more ways to go from one time-frequency zone to another, e.g., taking the Fourier transform of the vectors in zone VI moves them to zone III). In conclusion, it can be expected that possible combinations of $\Delta_t$, $N\Delta_f$ are confined to the spade-like region outlined by the black dots (and open circles) in FIG. 15.

The Uncertainty Principle for Nonzero Mean Time and Frequency.

If the reference time $t_R$ in Eq. 19 is allowed to be nonzero, then $$\Delta_t^2 = r_t^2 x^H (\Omega - \omega^{t_R} I)^H (\Omega - \omega^{t_R} I) x / \|x\|^2, \text{ or}$$

$$\Delta_t \equiv r_t \|(\Omega - \omega^{t_R} I) x\| / \|x\| \quad (B16)$$

Similarly, for nonzero reference frequency $f_R \equiv n_R/N$, $$\Delta_f \equiv r_f \|(\Omega - \omega^{n_R} I) F x\| / \|x\| = r_f \|(T^{-1} - \omega^{n_R} I) x\| / \|x\| \quad (B17)$$

Let $A_R \equiv \Omega - \omega^{t_R} I$, $B_R \equiv T^{-1} - \omega^{n_R} I$ and $$C_R \equiv r_t \begin{bmatrix} A_R \\ B_R \end{bmatrix}$$

When C is still defined with respect to $t_R = 0$ and $f_R = 0$, then $C_R^H C_R$ and $C^H C$ turn out to be similar, $$(C_R^H C_R) T^{t_R} \Omega^{n_R} = T^{t_R} \Omega^{n_R} (C^H C) \quad (B18)$$

This is readily shown using the relation $T^k \Omega^n = \omega^{-nk} \Omega^n T^k$, which is valid for any integer k, n. So, if $(\sigma^2, v)$ is an eigenvalue-eigenvector pair of $C^H C$, then $$(C_R^H C_R) T^{t_R} \Omega^{n_R} v = \sigma^2 T^{t_R} \Omega^{n_R} v \quad (B19)$$

meaning that $T^{t_R} \Omega^{n_R} v$ is an eigenvector of $C_R^H C_R$ with eigenvalue $\sigma^2$. It follows that the uncertainty of $T^{t_R} \Omega^{n_R} v$ relative to $t_R$ in the time domain and $f_R$ in the frequency domain is equal to the uncertainty of v relative to zero in both domains. This is no surprise. The squared absolute values (the 'weights') of the components of $T^{t_R} \Omega^{n_R} v$ are identical to those of v, albeit after a circular shift in the frequency domain (by $\Omega^{n_R}$) and in the time domain (by $T^{t_R}$).

Derivation of the Time-Frequency Transform

The columns of the time-frequency transform matrix M are orthonormal, $$M^H M = I \quad (C1)$$

This can be proved as follows. The product can be written as a sum of circulant matrices, $$M^H M = \frac{1}{M} [M_0^H \ \ldots \ M_{M-1}^H] \begin{bmatrix} M_0 \\ \vdots \\ M_{M-1} \end{bmatrix} \quad (C2)$$

$$= \frac{1}{M} \sum_{m=0}^{M-1} M_m^H M_m.$$

Since postmultiplication of $h_m^H$ by $T^{-1}$ means that its components are circularly shifted to the right, the circulant $M_m$ can also be written $$M_m = \begin{bmatrix} h_m^H \\ h_m^H T^{-1} \\ \vdots \\ h_m^H T^{-N+1} \end{bmatrix}. \quad (C3)$$

Since circulants are normal matrices, they commute with their Hermitian transpose, $$M_m^H M_m = M_m M_m^H \quad (C4)$$

$$= \begin{bmatrix} h_m^H \\ h_m^H T^{-1} \\ \vdots \\ h_m^H T^{-1N+1} \end{bmatrix} [h_m \ Th_m \ \ldots \ T^{N-1} h_m]$$

$$= \begin{bmatrix} h_m^H h_m & h_m^H T h_m & h_m^H T^2 h_m & \ldots & h_m^H T^{N-1} h_m \\ h_m^H T^{N-1} h_m & h_m^H h_m & h_m^H T h_m & \ldots & h_m^H T^{N-2} h_m \\ \vdots & & & & \end{bmatrix}$$

$$= circ\{g_m^H\},$$

where $g_m \equiv \{h_m^H h_m \ h_m^H T^{-1} h_m \ \ldots \ h_m^H T^{-N+1} h_m\}$ is the 'complex autocorrelation' of $h_m$.

Its components are $$g_{m,u} \equiv \begin{cases} h_m^H T^{-u} h_m, & 0 \leq u \leq M-1, \text{ or} \\ & N-M+2 \leq u \leq N-1; \\ 0, & \text{otherwise.} \end{cases} \quad (C5)$$

According to the definition of the N-vector $h_m$ (Eqs. 26 and 27), it can also be written as $\Omega^{mN/M} h_0$. Using $T^k \Omega^n = \omega^{-nk} \Omega^n T^k$, it follows that the nonzero components are equal to $$h_m^H T^{-u} h_m = \quad (C6)$$

$$h_0^H \Omega^{-mN/M} T^{-u} \Omega^{mN/M} h_0 = \omega^{muN/M} h_0^H T^{-u} h_0 = e^{2\pi i mu/M} a_u,$$

where $a_u \equiv h_0^H T^{-u} h_0$. When these components are summed over m, we have $$\sum_{m=0}^{M-1} g_{m,u} = \sum_{m=0}^{M-1} e^{2\pi i mu/M} a_u = \begin{cases} a_0 M, & u = 0; \\ 0, & \text{otherwise,} \end{cases} \quad (C7)$$

which follows from the fact that $\{e^{2\pi i mu/M}\}$ is a geometric progression for $m = 0, \ldots, M-1$. Note that $a_0 = h_0^H T^0 h_0 = \|h_0\|^2 = 1$ since $h_m$ is taken to be a unit vector. As a result, the sum in Eq. C2 can be rewritten as $$\frac{1}{M} \sum_{m=0}^{M-1} M_m^H M_m = \quad (C8)$$

$$\frac{1}{M} \sum_{m=0}^{M-1} circ\{g_m^H\} = \frac{1}{M} circ\left\{\sum_{m=0}^{M-1} g_m^H\right\} = \frac{1}{M} circ\{M, 0, \ldots, 0\} = I,$$

which completes the proof of Eq. C1.

The orthonormality property (Eq. C1) still holds if $h_0$ is approximated by a truncated normalized Gaussian with uncertainty $\Delta_t$ and $M' = 10 \cdot \Delta_t$ nonzero components (using Eq. B4), since it does not depend on the choice of $h_0$ (provided $\|h_0\| = 1$).

Time-Frequency Synthesis.

A direct corollary of the orthonormality property is that a given time series vector x can be written as the weighted sum of short-lasting oscillations (Eq. 34). Using the definition of Eq. 28, $$x = Ix = M^H M x = \qquad (C9)$$

$$\frac{1}{M}\sum_{m=0}^{M-1} M_m^H M_m = \frac{1}{M}\sum_{m=0}^{M-1} [h_{m,0} \ldots h_{m,N-1}] \begin{bmatrix} h_{m,0}^H \\ \vdots \\ h_{m,N-1}^H \end{bmatrix} =$$

$$\frac{1}{M}\sum_{m=0}^{M-1}\sum_{t=0}^{N-1} h_{m,t} h_{m,t}^H x = \frac{1}{M}\sum_{m=0}^{M-1}\sum_{t=0}^{N-1} h_{m,t} \tilde{x}_{m,t}.$$

Analysis of Variance in the Time-Frequency Domain

Another direct corollary of the orthonormality property of the TFT is that the 'energy' (the squared norm) of the N-vector x is preserved after the transformation, $$\|x\|^2 = x^H I x = x^H M^H M x = \|Mx\|^2 = \|\tilde{x}\|^2 \qquad (D1)$$

This permits an 'analysis of variance' (ANOVA) in the time-frequency domain. The above also means that the energy of x can be partitioned into M frequency-dependent components, $$\|x\|^2 = \frac{1}{M} x^H \left(\sum_{m=0}^{M-1} M_m^H M_m\right) x = \qquad (D2)$$

$$\frac{1}{M}\sum_{m=0}^{M-1} x^H M_m^H M_m x = \frac{1}{M}\sum_{m=0}^{M-1} \|M_m x\|^2 = \frac{1}{M}\sum_{m=0}^{M-1} \|\tilde{x}_m\|^2.$$

Suppose the random N-vector X has a multivariate normal distribution with expectation $E\{X\}=0$ and variance $\text{var}\{X\}=\sigma^2 I$. Then the quadratic form $\|X\|^2/\sigma^2$ follows a chi-square distribution on N degrees of freedom. According to Eq. D2, $\|X\|^2$ can be partitioned into M frequency-dependent components $\|\tilde{X}_m\|^2$. The quadratic form $\|\tilde{X}_m\|^2/N$ may be called the 'TFT sample power spectrum' of X for frequency $f_m$. For white noise, the expectation of this RV is $$E\{\|\tilde{X}_m\|^2/N\} = E\{\|M_m X\|^2\}/N = E\{X^H M_m^H M_m X\}/N$$

$$\sigma^2 \text{tr}\{M_m^H M_m\}/N,$$

where $\text{tr}\{\bullet\}$ stands for the trace of the matrix. Using Eq. C4, it follows that $\text{tr}\{M_m^H M_m\} = N h_m^H h_m = N$, so that $$E\{\|\tilde{X}_m\|^2/N\} = \sigma^2 \qquad (D3)$$

The sample power spectrum according to the definition above is however sensitive to bias due to the circularity assumption. Note that the components of $\tilde{X}_m \equiv M_m X$ are derived from X by circular convolution with a linear time-invariant filter with M nonzero elements (Eqs. 26-31). The structure of this filter is such that the first M−K−1 and the last K components of $\tilde{X}_m$ are dependent on the circularity assumption (provided these integers are larger than zero), where K is the largest integer less than or equal to M/2. A power estimator free of bias due to the circularity assumption is thus obtained with the 'selection matrix' S, defined as $$S \equiv \text{diag}\{\underbrace{0,\ldots,0}_{M-K-1}, \underbrace{1,\ldots,1}_{N-M+1}, \underbrace{0,\ldots,0}_{K}\} \qquad (D4)$$

Premultiplication of $\tilde{X}_m$ by S selects the components of $\tilde{X}_m$ that are independent of the circularity assumption, which gives the unbiased quadratic form $\|S M_m X\|^2$. When the complementary frequency $f_{M-m}$' is also included, the 'total' unbiased sample power may be defined as $$P_{X,m} \equiv \begin{cases} \|S M_m X\|^2 / N_S, & m = 0 \text{ or } m = \frac{1}{2}; \\ \|S(M_m + M_{M-m}) X\|^2 / (2 N_S), & \text{otherwise.} \end{cases} \qquad (D5)$$

The number of 'samples' in the t-f domain is $N_S = N - M + 1$.

The sample power (divided by $\sigma^2$) follows an approximate chi-square distribution with equivalent degrees of freedom (EDOFs)

$$\eta = 2 \cdot (E\{P_{X,m}\})^2 / \text{var}\{P_{X,m}\} \qquad (D6)$$

Letting $P \equiv S(M_m + M_{M-m})/(2 N_S)$ for $m \neq 0$ and $m \neq \frac{1}{2}$, it follows that for zero mean white noise X, $$E\{P_{X,m}\} = \sigma^2 \text{tr}\{P^H P\}, \qquad (D7)$$

$$\text{var}\{P_{X,m}\} = 2\sigma^4 \text{tr}\{(P^H P)^2\},$$

which gives $$\eta = (\text{tr}\{P^H P\})^2 / \text{tr}\{(P^H P)^2\} \qquad (D8)$$

In the present paper, $\eta$ was numerically computed according to Eq. D8 using mathematical computer software.

Derivation of Confidence Limits

Mean and variance of $\hat{B}_{Q,t,m}$ and $\hat{B}_{P,t,m}$. Since the noise in flow $\tilde{Q}_{e,t,m}$ is assumed to be zero mean white noise, the expectation of $\tilde{Q}_{t,m}$ is, using Eq. 43, $$E\{\tilde{Q}_{t,m}\} = E\{\tilde{x}_{t,m} b_{Q,t,m} + \tilde{Q}_{e,t,m}\} = \qquad (E1)$$

$$E\{\tilde{x}_{t,m} b_{Q,t,m}\} + E\{\tilde{Q}_{e,t,m}\} = \tilde{x}_{t,m} b_{Q,t,m} + 0 = \tilde{x}_{t,m} b_{Q,t,m}.$$

The variance of $\tilde{Q}_{e,t,m}$ is $\sigma_{Q,m}^2 I$. Since the product $\tilde{x}_{t,m} b_{Q,t,m}$ is deterministic, $$\text{var}\{\tilde{Q}_{t,m}\} = \text{var}\{\tilde{x}_{t,m} b_{Q,t,m} + \tilde{Q}_{e,t,m}\} = \text{var}\{\tilde{Q}_{e,t,m}\} = \sigma_{Q,m}^2 I \qquad (E2)$$

The mean and variance of $\hat{B}_{Q,t,m}$ now follow from Eq. 46, $$E\{\hat{B}_{Q,t,m}\} = E\{\tilde{x}_{t,m}^H \tilde{Q}_{t,m} / \|\tilde{x}_{t,m}\|^2\} = \qquad (E3)$$

$$\tilde{x}_{t,m}^H E\{\tilde{Q}_{t,m}\} / \|\tilde{x}_{t,m}\|^2 = \tilde{x}_{t,m}^H \tilde{x}_{t,m} b_{Q,t,m} / \|\tilde{x}_{t,m}\|^2 = b_{Q,t,m},$$

$$\text{var}\{\hat{B}_{Q,t,m}\} \frac{\tilde{x}_{t,m}^H}{\|\tilde{x}_{t,m}\|^2} \text{var}\{\tilde{Q}_{t,m}\} \frac{\tilde{x}_{t,m}}{\|\tilde{x}_{t,m}\|^2} = \qquad (E4)$$

$$\frac{\tilde{x}_{t,m}^H}{\|\tilde{x}_{t,m}\|^2} \cdot \sigma_{Q,m}^2 I \cdot \frac{\tilde{x}_{t,m}}{\|\tilde{x}_{t,m}\|^2} = \frac{\sigma_{Q,m}^2}{\|\tilde{x}_{t,m}\|^2}$$

As a result, $\hat{B}_{Q,t,m}$ is an unbiased estimator of $b_{Q,t,m}$. Mean and variance for $\hat{B}_{P,t,m}$ follow in an analogous manner, $$E\{\hat{B}_{P,t,m}\} = b_{P,t,m} \text{ and } \text{var}\{\hat{B}_{P,t,m}\} = \sigma_{P,m}^2 / \|\tilde{x}_{t,m}\|^2 \qquad (E5)$$

Confidence Limits.

The confidence limits for $\hat{B}_{Q,t,m}$ and $\hat{B}_{P,t,m}$ follow from the standard approach in least squares analysis. Combination of Eqs. 43 and 44 gives $$\tilde{Q}_{e,t,m} = \tilde{Q}_{t,m} - \tilde{x}_{t,m} b_{Q,t,m} = \tilde{x}_{t,m}(\hat{B}_{Q,t,m} - b_{Q,t,m}) + \hat{Q}_{e,t,m} \qquad (E6)$$

Due to the orthogonality between $\tilde{x}_{t,m}$ and $\hat{Q}_{e,t,m}$ (see FIG. 5), $$\|\tilde{Q}_{e,t,m}\|^2 = \|\tilde{x}_{t,m}\|^2 \cdot |\hat{B}_{Q,t,m} - b_{Q,t,m}|^2 + \|\hat{Q}_{e,t,m}\|^2 \quad (E7)$$

The random variable $\|\tilde{x}_{t,m}\|^2 |\hat{B}_{Q,t,m} - b_{Q,t,m}|^2/\sigma_{Q,m}^2$ has the form $$(\hat{B}_{Q,t,m} - E\{\hat{B}_{Q,t,m}\})^H (\text{var}\{\hat{B}_{Q,t,m}\})^{-1} (\hat{B}_{Q,t,m} - E\{\hat{B}_{Q,t,m}\})$$

and is thus (exactly) distributed as a chi-square variable (on one degree of freedom). When $\tilde{x}_{t,M-m}$ at the complementary frequency $f_{M-m} = 1 - m/M$ is also included in the estimation, the resulting chi-square variable has two degrees of freedom. When the noise is estimated by the total unbiased power spectrum (Eq. D5), Equation E7 decomposes the total power of the noise into orthogonal components with EDOFs $\eta = 2 + (\eta - 2)$. Then the ratio of the two orthogonal components at the right-hand side of Eq. E7 follows an F-distribution on $(2, \eta - 2)$ degrees of freedom. Let the upper $100(1-\alpha)$ % point of this distribution be denoted by $F_\alpha$. Then $$\frac{\|\tilde{x}_{t,m}\|^2 |\hat{B}_{Q,t,m} - b_{Q,t,m}|^2}{\|\hat{Q}_{e,t,m}\|^2} \leq F_\alpha \frac{2}{\eta - 2} \quad (E8)$$

Using the definition of the TFT sample coherence (Eq. 45) and assuming that $K_{Q,t,m}^2 > 0$, this can be rewritten as $$\frac{|\hat{B}_{Q,t,m} - b_{Q,t,m}|^2}{|b_{Q,t,m}|^2} \leq F_\alpha \frac{2}{\eta - 2} \frac{1 - K_{Qx,t,m}^2}{K_{Qx,t,m}^2} \quad (E9)$$

Denoting the right-hand side of this inequality by $A_{Q,t,m}^2$, $$|\hat{B}_{Q,t,m} - b_{Q,t,m}|^2 \leq |\hat{B}_{Q,t,m}|^2 A_{Q,t,m}^2 \quad (E10)$$

The $100(1-\alpha)$ % confidence region for $\hat{B}_{Q,t,m}$ is thus described by a circle in the complex plane with center $\hat{B}_{Q,t,m}$ and radius $|\hat{B}_{Q,t,m}|A_{Q,t,m}$. The confidence region for $\hat{B}_{P,t,m}$ is derived in a similar manner, $$|\hat{B}_{P,t,m} - b_{P,t,m}|^2 \leq |\hat{B}_{P,t,m}|^2 A_{P,t,m}^2 \quad (E11)$$

To arrive at a confidence region for $\hat{Z}_{t,m}$, multiply both sides of Eq. 10 by $|\hat{Z}_{t,m}/b_{Q,t,m}|^2$ and substitute $U \equiv \hat{Z}_{t,m} \hat{B}_{Q,t,m}/b_{Q,t,m}$, which gives $$|U - \hat{Z}_{t,m}|^2 \leq |U|^2 A_{Q,t,m}^2 \quad (E12)$$

Using the real and imaginary parts of the complex variables, this can be rearranged into $$\left| U - \frac{\hat{Z}_{t,m}}{1 - A_{Q,t,m}^2} \right|^2 \leq \left| \frac{\hat{Z}_{t,m}}{1 - A_{Q,t,m}^2} \right|^2 A_{Q,t,m}^2 \quad (E13)$$

Next divide both sides of Eq. E11 by $|b_{Q,t,m}|^2$. Replacing $\hat{B}_{P,t,m}$ by $\hat{Z}_{t,m} \hat{B}_{Q,t,m}$ (Eq. 47) and $\hat{Z}_{t,m} \hat{B}_{Q,t,m}/b_{Q,t,m}$ by U, $$|U - z_{t,m}|^2 \leq |U|^2 A_{P,t,m}^2 \quad (E14)$$

The confidence region for $\hat{Z}_{t,m}$ can now be derived in a two-step approach. According to Eq. E13, U lies within a circle with center $C_u \equiv \hat{Z}_{t,m}/(1 - A_{Q,t,m}^2)$ and radius $r_u \equiv |\hat{Z}_{t,m}| A_{Q,t,m}/(1 - A_{Q,t,m}^2)$, on $100(1-\alpha)$% of occasions (FIG. 16A). Suppose that $\tilde{Q}_{e,t,m}$ and $\tilde{P}_{e,t,m}$ are uncorrelated. Then, for a given value of U, $z_{t,m}$ lies within a second circle, with center U and radius $|U|A_{P,t,m}$, on $100(1-\alpha)$ % of occasions (Eq. E14). Consider the two extreme values for |U|, which are the magnitudes of $U_{min}$ and $U_{max}$ in FIG. 16A. The corresponding extreme values for $|z_{t,m}|$ are the magnitudes of $z_{min}$ and $z_{max}$ in FIG. 16B. From Eqs. E13 and E14, $$z_{min} = \hat{Z}_{t,m} \frac{1 - A_{P,t,m}}{1 + A_{Q,t,m}}, \quad (E15)$$

$$z_{max} = \hat{Z}_{t,m} \frac{1 + A_{P,t,m}}{1 - A_{Q,t,m}}$$

A conservative limit of the $100(1-\alpha)$ % confidence region for $\hat{Z}_{t,m}$ is now given by the circle that contains $z_{min}$ and $z_{max}$, and whose center lies on the line through $\hat{Z}_{t,m}$ and the origin. As a result, the corresponding confidence region is described by $$\left| z_{t,m} - \hat{Z}_{t,m} \frac{1 + A_{Q,t,m} A_{P,t,m}}{1 - A_{Q,t,m}^2} \right|^2 \leq \left| \hat{Z}_{t,m} \frac{A_{Q,t,m} + A_{P,t,m}}{1 - A_{Q,t,m}^2} \right|^2 \quad (E16)$$

This region is delimited by the circle in FIGS. 16B and 16C with center $C_2 \equiv \hat{Z}_{t,m}(1 + A_{Q,t,m} A_{P,t,m})/(1 - A_{Q,t,m}^2)$ and radius $r_2 \equiv |\hat{Z}_{t,m}|(A_{Q,t,m} + A_{P,t,m})/(1 - A_{Q,t,m}^2)$. This circle is not concentric about $\hat{Z}_{t,m}$. The distribution of possible values for $z_{t,m}$ for a given $\hat{Z}_{t,m}$ is skew-symmetric about $\hat{Z}_{t,m}$ (FIG. 16D). The skewness is expressed by $\tan \beta$ in FIG. 16C. From Eq. E16, it follows that $$\tan \beta = |C_2 - \hat{Z}_{t,m}|/r_2 = A_{Q,t,m} \quad (E17)$$

Special Case 1: No Noise Inflow.

If the noise in flow is zero, $\tilde{Q}_{e,t,m} = 0$, then $\tilde{Q}_{t,m} = \tilde{x}_{t,m} b_{Q,t,m}$ and $\hat{B}_{Q,t,m} = b_{Q,t,m}$ (Eqs. 43 and 46). Let the corresponding estimator of $z_{t,m}$ be denoted by $\hat{Z}_{t,m}^{(Q)}$. Assuming that $b_{Q,t,m} \neq 0$, $$\hat{Z}_{t,m}^{(Q)} = \frac{\hat{B}_{P,t,m}}{\hat{B}_{Q,t,m}} = \frac{\tilde{x}_{t,m}^H \tilde{P}_{t,m}}{\|\tilde{x}_{t,m}\|^2 b_{Q,t,m}}$$

Since in this case $\tilde{x}_{t,m} = \tilde{Q}_{t,m}/b_{Q,t,m}$, $$\hat{Z}_{t,m}^{(Q)} = \frac{\tilde{Q}_{t,m}^H \tilde{P}_{t,m}}{\|\tilde{Q}_{t,m}\|^2} \quad (E18)$$

This is the 'ordinary least squares estimator'. Then $K_{Qx,t,m}^2 = 1$ and $A_{Q,t,m} = 0$. The confidence limits are still described by Eq. E16, although with $A_{Q,t,m} = 0$. The confidence circle is centered about $\hat{Z}_{t,m}^{(Q)}$ now, with radius $|\hat{Z}_{t,m}^{(Q)}|A_{P,t,m}$. The skewness parameter $\tan \beta$ is equal to zero.

Special Case 2: No Noise in Pressure.

If the noise in pressure is zero, $\tilde{P}_{e,t,m} = 0$, then $\tilde{P}_{t,m} = \tilde{x}_{t,m} b_{P,t,m}$ and $\hat{B}_{P,t,m} = b_{P,t,m}$. When the corresponding estimator of $z_{t,m}$ is denoted by $\hat{Z}_{t,m}^{(P)}$, $$\hat{Z}_{t,m}^{(P)} = \frac{\hat{B}_{P,t,m}}{\hat{B}_{Q,t,m}} = \frac{b_{P,t,m}\|\tilde{x}_{t,m}\|^2}{\tilde{x}_{t,m}^H \tilde{Q}_{t,m}} = \frac{\|\tilde{P}_{t,m}\|^2}{\tilde{P}_{t,m}^H \tilde{Q}_{t,m}} \quad (E19)$$

This is the 'data least squares estimator'. Now $K_{Px,t,m}^2 = 1$ and $A_{P,t,m} = 0$. From Eq. E16, the confidence circle has center $\hat{Z}_{t,m}^{(P)}/(1 - A_{Q,t,m}^2)$ and radius $|\hat{Z}_{t,m}^{(P)}|/(1 - A_{Q,t,m}^2)$. The skewness parameter tan β equals $A_{Q,t,m}$. The two estimators $\hat{Z}_{t,m}^{(Q)}$ and $\hat{Z}_{t,m}^{(P)}$ are related through the squared coherence between flow and pressure, $$K_{PQ,t,m}^2 \equiv \frac{|\tilde{Q}_{t,m}^H \tilde{P}_{t,m}|^2}{\|\tilde{Q}_{t,m}\|^2 \|\tilde{P}_{t,m}\|^2} = \frac{\tilde{Q}_{t,m}^H \tilde{P}_{t,m}}{\|\tilde{Q}_{t,m}\|^2} \cdot \frac{\tilde{P}_{t,m}^H \tilde{Q}_{t,m}}{\|\tilde{P}_{t,m}\|^2} = \frac{\hat{Z}_{t,m}^{(Q)}}{\hat{Z}_{t,m}^{(P)}} \quad (E20)$$

Examples

Squared Coherences as a Function of Time and Frequency

Figure 17:
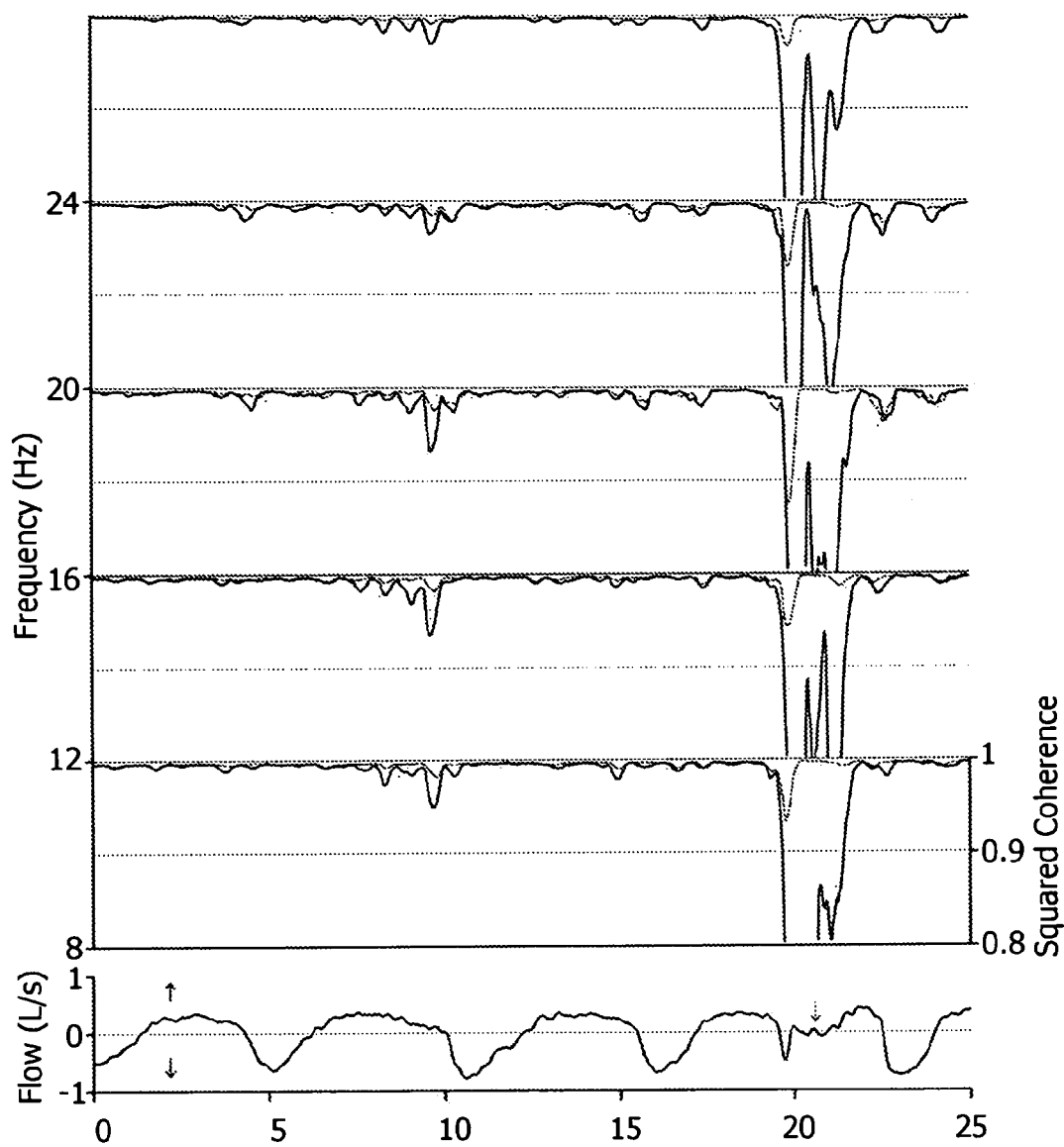
FIG. 17 illustrates the squared coherence as a function of time and frequency for a healthy subject.
Figure 18:
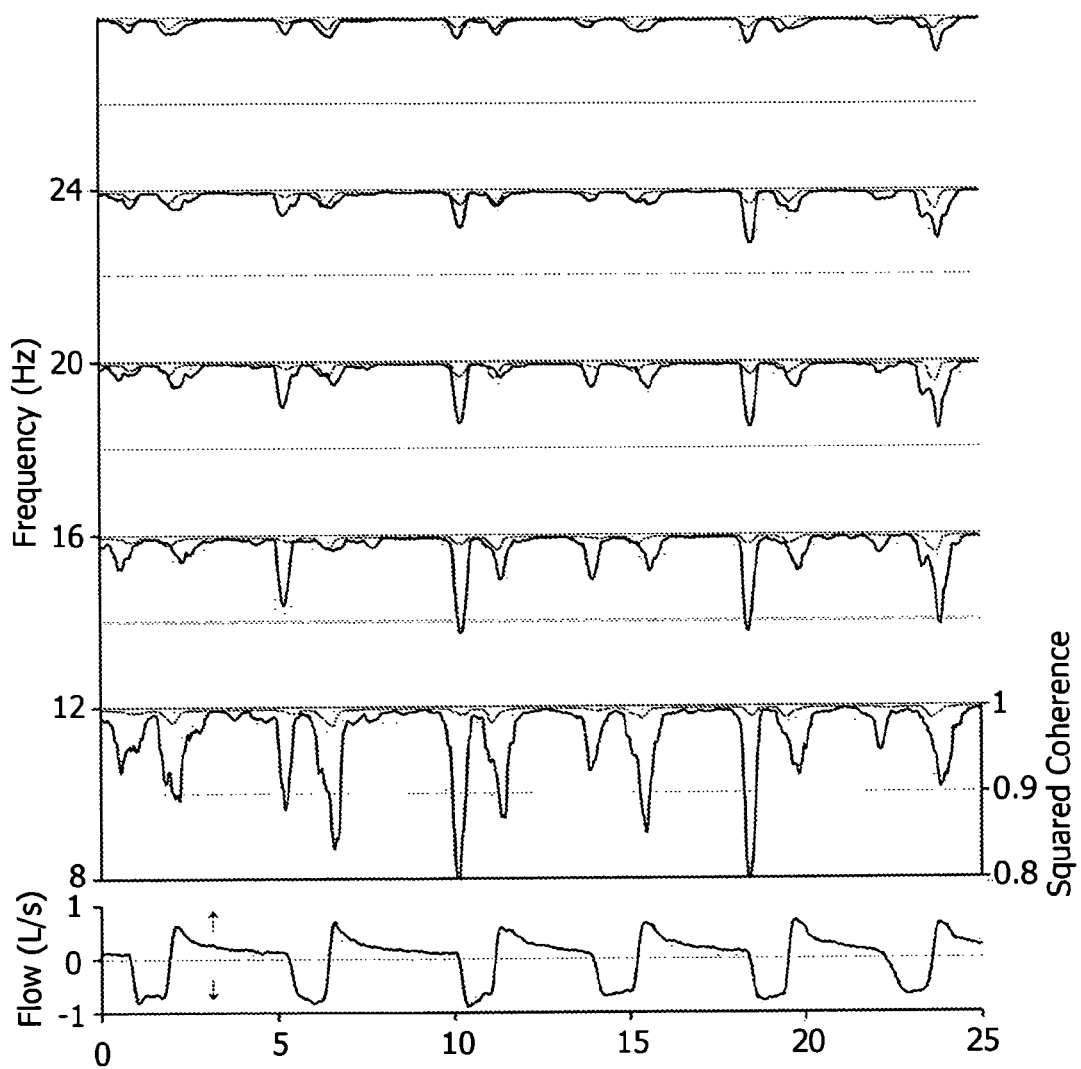
FIG. 18 illustrates the squared coherence as a function of time and frequency for a subject with COPD.

FIG. 17 shows the squared coherences for the same recording as in FIG. 7. In this example, the coherence between loudspeaker input and flow was generally lower than the coherence between input and pressure. As is apparent from the figure, the coherences change as a function of both time and frequency. The smallest coherences are obtained at the turning points from inspiration to expiration and vice versa, and at the lowest frequencies. Swallowing has a deep impact on coherence, especially between input and flow. FIG. 18 shows the squared coherences as a function of time and frequency for the estimated impedance shown in FIG. 8 for a patient with COPD. The drops in coherence at the turning points between the respiratory phases are much more pronounced than in the normal example of FIG. 17. In both FIGS. 17 and 18, the bold lines represent the squared coherence $K_{Qx,t,m}^2$ between loudspeaker input and flow as a function of time for different resonant frequencies (8 to 24 Hz) and the thin lines represent the squared coherence $K_{Px,t,m}^2$ between loudspeaker input and pressure. "Flow" represents the low-frequency component of airflow, "insp" represents inspiration and "exp" represents expiration.

In conclusion, a method is presented to estimate the transfer function of the respiratory system of a subject with optimal time-frequency resolution.

As described above, the estimate of respiratory impedance may be made by a diagnostic tool that uses the estimate to assess obstruction of the airways or to estimate the severity of disease. The diagnostic tool may therefore also be used to assess the effectiveness of treatments (whether pharmacological or otherwise) that should affect the respiratory impedance.

For example, the estimates of respiratory impedance can be used to detect (i) expiratory flow limitation in chronic obstructive lung disease (COPD); (ii) the severity of airway obstruction in COPD or asthma, which itself be used to evaluate the effect of inhaled airway dilators (e.g. sympathicomimetic or parasympathicolytic drugs) over the course of time (this can be applicable to a research setting and also to a clinical setting where the patient is unable to perform the standard forced respiratory maneuvers; (iii) airway obstruction in asthma or COPD during sleep; or (iv) upper airway obstruction during sleep in patients suspected of sleep apnea-hypopnea syndrome.

The estimates of respiratory impedance may also or alternatively be used to adapt the settings of machine used in the treatment of a medical condition. For example, the estimates of respiratory impedance can be used in the adjustment of settings of noninvasive ventilation in COPD. The respiratory impedance can be used as an input to the ventilator to provide information on the severity of the airway impedance on a continuous basis (with unreliable values, as indicated by the confidence values, being discarded). This information can also be used to adjust the level of bilevel positive airway pressure with which the expiratory flow limitation is just overcome. As an alternative example, the estimates of respiratory impedance can be used as an aid to guide the level of continuous positive airway pressure in patients with obstructive sleep apnea syndrome.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

REFERENCES

1. Dellacà et al. Expiratory flow limitation detected by forced oscillation and negative expiratory pressure, European Respiratory Journal Vol. 29 No. 2, pages 363-374
2. Daróczy B, Hantos Z. An improved forced oscillation estimation of respiratory impedance. *Int J Biomed Comput* 13: 221-235, 1982.
3. Forbes G W, Alonso M A. Consistent analogs of the Fourier uncertainty relation. *Am J Physics* 69: 340-347, 2001.
4. Forbes G W, Alonso M A, Siegman A E. Uncertainty relations and minimal uncertainty states for the discrete Fourier transform and the Fourier series. *J Phys A: Math Gen* 36: 7027-7047, 2003.
5. Gabor D. Theory of communications. *J Inst Electr Eng* 93: 429-457, 1946.

Table 1.
Symbols and Abbreviations.
Time and Frequency
  $f_m$, $f_n$ discrete frequency m/M (or n/N)
  $f_R$ reference frequency for $\Delta_f$
  $f_n$ N-vector that describes an harmonic oscillation with frequency $f_n$
  m frequency index for the TFT
  M (M') width of the TFT filter (or effective width using a truncated Gaussian)
  n frequency index for the ODFT
  N number of events in a time series
  $N_S$ number of samples in the t-f domain from a stochastic process
  $r_t$, $r_f$ radius of the time circle (or frequency circle)
  t discrete time index
  $t_R$ reference time for $\Delta_t$ A, B, C matrices related to uncertainty in time and frequency
F ODFT matrix
M ($M_m$) TFT matrix (or partial TFT matrix for frequency $f_m$)
T time-shift operator; circ$\{0, \ldots, 0, 1\}$
$\Delta_t$, $\Delta_f$ uncertainty in time or frequency
$\omega$ complex exponential; $\exp(2\pi i/N)$
$\sigma_{min}$, $\sigma_{max}$ minimal and maximal singular value of C
$\Omega$ diagonal matrix with $\omega^t$ on the main diagonal; diag$\{\omega^0, \ldots, \omega^{N-1}\}$
Names of Variables
  p pressure
  q flow
  x loudspeaker input (or an unknown variable)
  z respiratory impedance

| Types of variables | Examples |
|---|---|
| deterministic variable as a function of discrete time | $q_t$ |
| random variable as a function of discrete time | $Q_t$ |
| deterministic N-vector (lowercase) | q |
| random N-vector (uppercase) | Q |
| vector in the t-f domain (centered about frequency $f_m$) | $\tilde{Q}_m$ |
| vector in the t-f domain (centered about frequency $f_m$ and starting at time t) | $\tilde{Q}_{t,m}$ |
| deterministic vector 'predicted' by linear regression in t-f domain | $\tilde{q}_{p,t,m}$ |
| random 'error' for linear regression in t-f domain | $\tilde{Q}_{e,t,m}$ |
| estimator of the error in t-f domain | $\hat{\tilde{Q}}_{e,t,m}$ |

Linear Filters
  $h_{qx}$ vector with the periodized impulse response of filter from x to q
  $H_{qx,n}$ transfer function from x to q for frequency $f_n$
  $C_{qx}$ circulant matrix that describes the filter between loudspeaker input and flow
  $\Lambda_{xq}$ diagonal matrix with $H_{qx,n}$ on the main diagonal
Statistics
  $A_{Q,t,m}$ variable in t-f domain that determines the contribution of noise in flow to the confidence region for $\hat{Z}_{t,m}$
  $F_\alpha$ upper $100(1-\alpha)\%$ confidence limit for the F-test on $(2, \eta-2)$ degrees of freedom
  $K_{Qx,t,m}^2$ squared sample coherence between loudspeaker input and flow in t-f domain
  $\hat{Z}_{t,m}$ bivariate least squares estimator of impedance $z_{t,m}$ as a function of time and frequency
  $\hat{Z}_{t,m}^{(Q)}$ estimator of $z_{t,m}$ under the assumption that the noise in flow is zero
  $\alpha$ type II error
  $\beta$ angle that determines the deviation of $\hat{Z}_{t,m}$ from the center of the confidence region
  $\eta$ equivalent degrees of freedom
  $\mu_Q$ mean flow
  $\sigma_Q^2$ variance of the noise in flow
General Mathematical Symbols
  i imaginary number ($i^2 = -1$)
  I N×N identity matrix
  $\equiv$ is by definition equal to
  $|x_t|$ I magnitude of complex-valued $x_t$
  $\|x\|$ 2-norm of N-vector x
  $x^H$ Hermitian transpose of the vector x
  $x^*$ complex conjugate of x
  $\{\bullet\}$ sequence (usually expressed as a column vector)
  diag$\{\bullet\}$ diagonal matrix with the sequence on the main diagonal
  circ$\{\bullet\}$ circulant matrix with the sequence in the first row Abbreviations
  FOT forced oscillation technique
  t-f domain time-frequency domain
  TFT time-frequency transform
  ODFT orthonormal discrete Fourier transform
  RV random variable

The invention claimed is:

1. A method of estimating respiratory impedance with a system comprising a patient interface device, an excitation source operatively coupled to the patient interface, a ventilator, and one or more hardware processors, the method comprising:
  coupling the patient interface device to an airway of a subject who is using the ventilator to create a pneumatic system that includes the patient interface device and an airway of such a subject;
  generating, with the excitation source, pressure oscillations, flow oscillations, or volume of gas oscillations in the airway of the subject;
  determining, with the one or more hardware processors, the flow and pressure of the gas in the pneumatic system to produce a respective time series representing the flow and the pressure;
  transforming, with the one or more hardware processors, the respective time series to the time-frequency domain to create a transformed time series, wherein the transforming determines flow and pressure as a function of discrete time and different frequencies, wherein the different frequencies are a function of a frequency index and an effective width of a time-frequency filter, and wherein the transforming is based on the frequency index, the time frequency filter, and a weighting factor that is approximated by a windowing function of time, the weighting factor being a function of a time uncertainty, wherein the time series of measurements for flow and pressure are denoted $q_t$ and $p_t$ respectively, and the step of transforming the respective time series to the time-frequency domain comprises evaluating $$\tilde{q}_{t,m} = \sum_{l=-K_1}^{K_1} w_l e^{-2\pi i m l / M} q_{t+l}$$

for the flow time series and $$\tilde{p}_{t,m} = \sum_{l=-K_1}^{K_1} w_l e^{-2\pi i m l / M} p_{t+l}$$

for the pressure time series, wherein the different frequencies are give by $f_m = m/M$, where m is the frequency index and M is the effective width of the time-frequency filter, $i^2 = -1$, and wherein the weighting factor $w_l$ is given by $w_l = e^{-(l/\Delta_t)^2}$, and $\Delta_t$ is the uncertainty in time;
  estimating, with the one or more hardware processors, power of the flow and the pressure from the transformed time series;
  estimating, with the one or more hardware processors, respective cross spectra of the flow and the pressure based the transformed time series;
  estimating, with the one or more hardware processors, the respiratory impedance of the subject from the estimated power and the estimated cross spectra; and providing, with the one or more hardware processors, input to the ventilator based on the estimated respiratory impedance, the provided input causing an adjustment of one or more settings of the ventilator.

2. A method as claimed in claim 1, wherein the step of estimating the respiratory impedance of the subject from the estimated power and the estimated cross spectra comprises:

determining transfer functions from the pressure oscillations to the flow and pressure respectively from the respective estimated power and estimated cross spectra; and estimating the respiratory impedance from the flow and pressure transfer functions.

3. A method as claimed in claim 1, wherein the method further comprises a step of determining confidence limits on the estimated impedance.

4. A method as claimed in claim 1, wherein the windowing function is a Gaussian function, a triangle function, a piece-wise linear approximation function, or a polynomial function.

5. A method as claimed in claim 1, wherein the step of estimating the power of the flow and pressure comprises evaluating $$P_{q,t,m} = \frac{1}{N_S} \sum_{l=-K_2}^{K_2} |\tilde{q}_{t+l,m}|^2$$

for the flow and $$P_{p,t,m} = \frac{1}{N_S} \sum_{l=-K_2}^{K_2} |\tilde{p}_{t+l,m}|^2$$

for the pressure, where $N_S$ is the number of samples in the time-frequency domain, $K_2=\frac{1}{2}(N_S-1)$ where $N_S$ is odd and $|\cdot|$ stands for the absolute value.

6. A method as claimed in claim 5, wherein the step of estimating the cross spectra of the flow and pressure with the generated pressure waves comprises evaluating $$C_{xq,t,m} = \frac{1}{N_S} \sum_{l=-K_2}^{K_2} \tilde{x}^*_{t,m} \tilde{q}_{t,m}$$

for the flow and $$C_{xp,t,m} = \frac{1}{N_S} \sum_{l=-K_2}^{K_2} \tilde{x}^*_{t,m} \tilde{p}_{t,m}$$

for the pressure, where the asterisk denotes the complex conjugate and $\tilde{x}_{t,m}$ represents the pressure waves.

7. A method as claimed in claim 6, wherein the step of estimating the respiratory impedance of the subject from the estimated power and cross spectra comprises determining a transfer function from the pressure waves to the flow by evaluating $$B_{xq,t,m} = \frac{C_{xq,t,m}}{P_{x,t,m}}$$

and a transfer function from the pressure waves to the pressure by evaluating $$B_{xp,t,m} = \frac{C_{xp,t,m}}{P_{x,t,m}},$$

and wherein the respiratory impedance is estimated by evaluating $$Zrs_{t,m} = \frac{B_{xp,t,m}}{B_{xq,t,m}}$$

with real component $Rrs_{t,m}$ and imaginary component $Xrs_{t,m}$.

8. A method as claimed in claim 7, further comprising a step of determining confidence limits on the estimated impedance which includes:

determining the squared coherence between the pressure waves and the flow using $$K^2_{xq,t,m} = \frac{|C_{xq,t,m}|^2}{P_{x,t,m} \cdot P_{q,t,m}};$$

determining the squared coherence between the pressure waves and the pressure using $$K^2_{xp,t,m} = \frac{|C_{xp,t,m}|^2}{P_{x,t,m} \cdot P_{p,t,m}};$$

determining the number of degrees of freedom, $\eta$, of the power and cross spectra;

determining a flow-related variable $A_{p,t,m}^2$ from $$A^2_{q,t,m} = F_\alpha\left(\frac{2}{\eta-2}\right)\left(\frac{1-K^2_{xq,t,m}}{K^2_{xq,t,m}}\right);$$

determining a pressure-related variable $A_{p,t,m}^2$ from $$A^2_{p,t,m} = F_\alpha\left(\frac{2}{\eta-2}\right)\left(\frac{1-K^2_{xp,t,m}}{K^2_{xp,t,m}}\right);$$

determining $100(1-\alpha)\%$ confidence limits for the real and imaginary parts of the estimated impedance from, respectively, $Rrs \cdot c_1 \pm c_2$ and $Xrs \cdot c_1 \pm c_2$, where $c_1 = 1 + A_{q,t,m} \cdot c_3$, $$c_2 = |Zrs_{t,m}| \cdot c_3 \text{ and } c_3 = \frac{A_{q,t,m} + A_{p,t,m}}{1 - A^2_{q,t,m}}.$$

9. A method as claimed in claim 7, further comprising the step of rejecting the estimates of respiratory impedance for a given time and frequency if either $A_{q,t,m} \geq$ a first threshold or $A_{p,t,m} \geq$ a second threshold.

10. A method as claimed in claim 9, wherein the first threshold is 1 and wherein the second threshold is 1.

11. A method as claimed in claim 1, wherein estimating the respective cross spectra of the flow and the pressure based the transformed time series is done based on a least squares criterion using a model with the oscillating pressure, flow, or volume of gas as an input and the flow and the pressure as outputs.

12. A method as claimed in claim 1, wherein determining the flow of the gas in the pneumatic system is accomplished by measuring the flow using a flow sensor operatively coupled to the pneumatic system, and wherein determining the pressure of the gas in the pneumatic system is accomplished using a pressure sensor operatively coupled to the pneumatic system.

13. An apparatus for estimating respiratory impedance of a subject, the apparatus comprising:
a patient interface device;
a ventilator;
an excitation source for generating pressure oscillations, flow oscillations, or volume of gas oscillations in the airway of the subject;
means for determining the flow and the pressure of gas in a pneumatic circuit defined by the patient interface device and an airway of such a subject and for outputting respective time series of values representing the flow or the pressure;
a processor configured to:
transform the respective time series to a time-frequency domain, wherein the transforming determines flow and pressure as a function of discrete time and different frequencies, wherein the different frequencies are a function of a frequency index and an effective width of a time-frequency filter, and wherein the transforming is based on the frequency index, the time frequency filter, and a weighting factor that is approximated by a windowing function of time the weighting factor being a function of a time uncertainty, wherein the time series of measurements for flow and pressure are denoted $q_t$ and $p_t$ respectively, and the step of transforming the respective time series to the time-frequency domain comprises evaluating $$\tilde{q}_{t,m} = \sum_{l=-K_1}^{K_1} w_l e^{-2\pi i m l/M} q_{t+l}$$

for the flow time series and $$\tilde{p}_{t,m} = \sum_{l=-K_1}^{K_1} w_l e^{-2\pi i m l/M} p_{t+l}$$

for the pressure time series, wherein the different frequencies are given by $f_m = m/M$, where m is the frequency index and M is the effective width of the time-frequency filter, $i^2 = -1$, and wherein the weighting factor $w_l$ is given by $w_l = e^{-(l/\Delta_t)^2}$, and $\Delta_t$ is the uncertainty in time;
estimate power of the flow and the pressure based on the respective transformed time series;
estimate respective cross spectra of the flow and pressure based the respective transformed time series;
estimate the respiratory impedance of the subject from the estimated power and cross spectra; and
provide input to the ventilator based on the estimated respiratory impedance, the provided input causing an adjustment of one or more settings of the ventilator.

14. An apparatus as claimed in claim 13, wherein the means for determining the flow and the pressure of gas in the pneumatic circuit comprises:
a flow sensor operatively coupled to the pneumatic system; and
a pressure sensor operatively coupled to the pneumatic system.

15. An apparatus as claimed in claim 13, wherein estimating the respective cross spectra of the flow and the pressure based the transformed time series is done based on a least squares criterion using a model with the oscillating pressure, flow, or volume of gas as an input and the flow and the pressure as outputs.

16. An apparatus as claimed in claim 13, wherein estimating the respiratory impedance of the subject from the estimated power and the estimated cross spectra comprises:
determining transfer functions from the pressure oscillations to the flow and pressure respectively from the respective estimated power and estimated cross spectra; and
estimating the respiratory impedance from the flow and pressure transfer functions.

17. An apparatus as claimed in claim 13, wherein the processor is further configured to determine confidence limits for the estimated respiratory impedance.

18. A method as claimed in claim 1, wherein providing the input to the ventilator comprises providing the estimated respiratory impedance as input to the ventilator to cause the adjustment of one or more settings of the ventilator based on the estimated respiratory impedance.

19. A method as claimed in claim 1, wherein providing the input to the ventilator comprising providing input to the ventilator on a continuous basis based on the estimated respiratory impedance to cause the ventilator to adjust positive airway pressure effectuated by the ventilator for the subject.

* * * * *